United States Patent
Horn et al.

(10) Patent No.: US 7,895,718 B2
(45) Date of Patent: Mar. 1, 2011

(54) FASTENING SYSTEM

(75) Inventors: Thomas Alexander Horn, Hofheim (DE); Mark James Kline, Okeana, OH (US); Kazuhiko Masuda, Ichihara (JP); Hisashi Morimoto, Ichihara (JP)

(73) Assignee: The Procter & Gamble Company, Cincinnati, OH (US)

( * ) Notice: Subject to any disclaimer, the term of this patent is extended or adjusted under 35 U.S.C. 154(b) by 1042 days.

(21) Appl. No.: 11/710,216

(22) Filed: Feb. 23, 2007

(65) Prior Publication Data
US 2008/0201919 A1    Aug. 28, 2008

(51) Int. Cl.
A44B 21/00    (2006.01)
B32B 3/06    (2006.01)

(52) U.S. Cl. ............ 24/442; 428/100; 24/444; 604/391

(58) Field of Classification Search ........... None
See application file for complete search history.

(56) References Cited

U.S. PATENT DOCUMENTS

| | | | |
|---|---|---|---|
| 3,860,003 A | 1/1975 | Buell |
| 3,911,173 A | 10/1975 | Sprague, Jr. |
| 3,929,135 A | 12/1975 | Thompson |
| 4,324,426 A | 4/1982 | Michelson |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,785,996 A | 11/1988 | Ziecker et al. |
| 4,834,735 A | 5/1989 | Alemany et al. |
| 4,842,666 A | 6/1989 | Werenicz |
| 4,888,231 A | 12/1989 | Angstadt |
| 4,892,536 A | 1/1990 | Desmarais et al. |

(Continued)

FOREIGN PATENT DOCUMENTS

EP    0 381 087 A1    8/1990

(Continued)

OTHER PUBLICATIONS

International Search Report.

*Primary Examiner* — Jack W. Lavinder
(74) *Attorney, Agent, or Firm* — Laura L. Whitmer

(57) ABSTRACT

A mechanical fastening system having an engaging component and a receiving component. The receiving component has a first bond line, a second bond line, a bond zone, and a plurality of consecutive sweep regions. The second bond line is disposed adjacent to the first bond line such that a portion of the second bond line overlaps a portion of the first bond line. The bond zone circumscribes the first bond line and the second bond line. The plurality of consecutive sweep regions are disposed within the bond zone. At least one sweep region includes a portion of both the first bond line and the second bond line, and the remaining sweep regions include at least a portion of the first or the second bond lines. The receiving component has a bond ratio greater than or equal to about 1 and less than or equal to about 20.

17 Claims, 12 Drawing Sheets

U.S. PATENT DOCUMENTS

| | | | |
|---|---|---|---|
| 4,909,803 A | 3/1990 | Aziz et al. | |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,260,345 A | 11/1993 | Desmarais et al. | |
| 5,269,755 A | 12/1993 | Bodicky | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,318 A | 3/1995 | Dreier | |
| 5,460,622 A | 10/1995 | Dragoo et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,865,823 A | 2/1999 | Curro | |
| 5,938,648 A | 8/1999 | LaVon et al. | |
| 5,941,864 A | 8/1999 | Roe | |
| 5,968,025 A | 10/1999 | Roe et al. | |
| 5,977,430 A | 11/1999 | Roe et al. | |
| 5,997,520 A | 12/1999 | Ahr et al. | |
| 6,013,063 A | 1/2000 | Roe et al. | |
| 6,168,584 B1 | 1/2001 | Allen et al. | |
| 6,680,422 B2 | 1/2004 | Roe | |
| 6,716,441 B1 | 4/2004 | Osborne et al. | |
| 2005/0009173 A1 | 1/2005 | Amand | |
| 2005/0125877 A1 | 6/2005 | Benjamin et al. | |
| 2005/0125923 A1 | 6/2005 | Benjamin et al. | |
| 2005/0129743 A1 | 6/2005 | Benjamin et al. | |
| 2005/0208260 A1* | 9/2005 | Baldauf | 428/95 |
| 2007/0007267 A1 | 1/2007 | Rayl et al. | |

FOREIGN PATENT DOCUMENTS

| | | |
|---|---|---|
| EP | 1 181 873 A1 | 2/2002 |
| EP | 1 279 348 A1 | 1/2003 |
| WO | WO-94/014395 A1 | 7/1994 |
| WO | WO-95/016746 A1 | 6/1995 |
| WO | WO-95/024173 A2 | 9/1995 |

* cited by examiner

FASTENING SYSTEM

FIELD OF THE INVENTION

The present invention pertains to fastening systems. Specifically, the present invention pertains to receiving components for use in conjunction with suitable engaging components in a fastening system.

This invention was made pursuant to a joint research agreement between The Procter & Gamble Company and Mitsui Chemicals Inc.

BACKGROUND OF THE INVENTION

Refastenable mechanical fastening systems can be used in a wide number of applications. For example, such refastenable fastening systems can be used to connect one portion of a disposable absorbent article to another portion of the disposable absorbent article.

In general, mechanical fastening systems comprise a receiving/female component and an engaging/male component. In some mechanical fastening systems, the engaging member comprises a plurality of hook elements, and the receiving component comprises a plurality of loop elements. In a fastened state, the hook elements typically are entangled with the loop elements such that a connection between the engaging and receiving components is formed.

Nonwoven webs are known in the art as potential materials for use as the female component. Typically, a nonwoven female component comprises a plurality of polymeric fibers. Portions of these fibers can be joined together by fiber-to-fiber bonds to form a web having sufficient available unbonded fibers or unbonded portions of bonded fibers and web integrity. The fiber-to-fiber bonds are typically formed by fusing portions fibers together via, for example, heat, pressure, or sound (i.e., ultrasonic) energy.

In some processes a pair of heated calendering rolls can be used to create these fiber-to-fiber bonds. Typically, one of the calendering rolls comprises a plurality of protrusions which extend outward from its outer surface. A constant force is generally applied to one of the calendering rolls such that as the nonwoven web passes between the calendering rolls, the protrusions apply pressure to the nonwoven web. In general, at the location of applied pressure, at least one fiber-to-fiber bond is created.

In general, nonwoven webs which are to be used as receiving components are not completely bonded, e.g. 100% fiber-to-fiber bonds. Because the fiber-to-fiber bonds typically render the bonded areas unengageable by an engaging component, bonding the nonwoven web completely can yield a poorly performing receiving component. Therefore, the protrusions extending outward from the outer surface of the calendering roll are typically spaced apart such that a particular bonding pattern is created in the nonwoven.

Additionally, it may be desirable to have large, open, unbonded areas to assure that wherever a hook from the engaging component is placed an unbonded fiber or an unbonded portion of a bonded fiber is available to engage the hook. However, a bond pattern creating large, open, unbonded areas can have reduced strength in a cross machine direction because of the reduced number of fiber-to-fiber bonds in the unbonded areas. To compensate, some bond patterns can create fully enclosed areas e.g. fully bonded fibers surrounding unbonded fibers. However, a bond pattern which creates fully bonded fibers surrounding unbonded fibers can reduce the likelihood that a hook from an engaging component will find an unbonded fiber with which it can engage.

Additionally, the bond pattern can negatively impact the quality of the fiber-to-fiber bonds. For, example because conventional bond patterns do not completely bond the nonwoven web, the pressure applied to the nonwoven web as the nonwoven web passes through the calendering rolls can fluctuate. In some cases, the pressure fluctuations can cause higher pressures at some fiber-to-fiber bond sites and cause lower pressures at other fiber-to-fiber bond sites. The higher pressure can result in overbonding or even cutting through fibers (which weakens the resulting web). The lower pressure may result in a reduced percentage of bonded area being formed compared to the desired percentage of bonded area, lower bond strength and/or lower bond quality. Additionally, the lower pressure may cause reduced strength in the cross machine direction.

Consequently, there is a need to provide a fastening system which includes a receiving component having a bond pattern which reduces the pressure fluctuations experienced by the receiving component during processing while maintaining sufficient areas of unbonded fibers and/or unbonded portions of bonded fibers.

SUMMARY OF THE INVENTION

The present invention pertains to a mechanical fastening system comprising an engaging component and a receiving component. The engaging component comprises a plurality of engaging elements. The receiving component has a longitudinal axis and a lateral axis, wherein the plurality of engaging elements are capable of engaging the receiving component.

The receiving component further comprises a first bond line, a second bond line, a bond zone, and a plurality of consecutive sweep regions. The first bond line and second bond line extend in a first direction, wherein the second bond line is disposed adjacent to the first bond line such that a portion of the second bond line overlaps a portion of the first bond line. The overlap is generally parallel to a second direction which is generally perpendicular to the first direction.

The bond zone circumscribes the first bond line and the second bond line. The plurality of consecutive sweep regions is disposed within the bond zone. Each sweep region extends in a direction generally parallel to the longitudinal axis, and each sweep region comprises a length and a width. The lengths of the sweep regions are equal, and the widths of the sweep regions are equal. At least one sweep region comprises a portion of both the first bond line and the second bond line, wherein the remaining sweep regions of the plurality of sweep regions comprise at least a portion of the first bond line or at least a portion of the second bond line. Each sweep region has a bonded area, and the receiving component has a bond ratio between two sweep regions which is greater than or equal to about 1 and less than or equal to about 20.

DETAILED DESCRIPTION OF THE INVENTION

Definitions

Figure 1A:
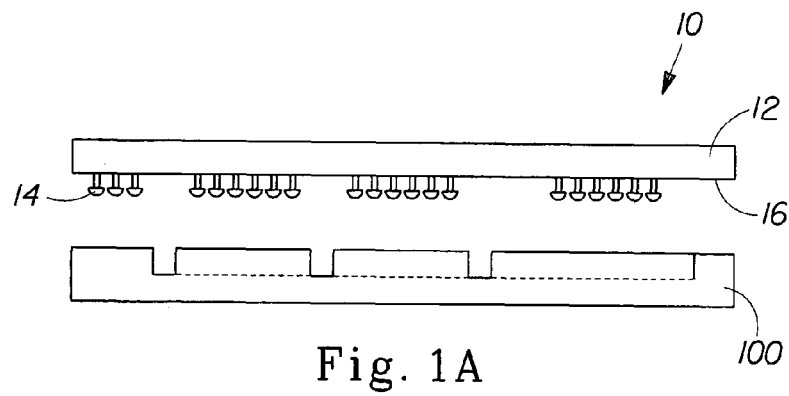
FIG. 1A is an elevation view showing a fastening system constructed in accordance with the present invention.

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

"Body-facing", "wearer-facing", "outer-facing", and "garment-facing", refer respectively to the relative location of an element or a surface of an element or group of elements. "Body-facing" and "wearer facing" imply the element or surface is nearer to the wearer during wear than some other element or surface. "Garment-facing" and "outer facing" imply the element or surface is more remote from the wearer during wear than some other element or surface (i.e., element or surface is proximate to the wearer's garments that may be worn over the disposable absorbent article).

As used herein, the term "bond line" refers to a plurality of sites on a substrate where the fibers of the substrate have been fused together. The plurality of sites can be fused together to form the "line". However, the term "line", as used herein, can also describe a series of discrete points or short lines closely spaced so as to effectively approximate a line. Therefore, those skilled in art will recognize that although a solid line bonding pattern is described, the benefits of the present invention can similarly be achieved by closely spaced points or discrete line segments which effectively approximate a line.

As used herein, the term "bond line pattern" refers to at least two bond lines which have some overlap between the at least two bond lines.

As used herein the term "consecutive" means following one after another. For example, adjacent sweep regions of the present invention may share boundaries with one another.

As used herein, the term "crimp" refers to a characteristic of a fiber having at least one fold or ridge. The term "crimp" includes fibers which have multiple folds, fibers which have curls, and/or fibers which form a spiral or helical structure.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable absorbent articles, a "longitudinal" direction runs substantially perpendicular from a waist edge to an opposing waist edge of the article and generally parallel to the maximum linear dimension of the article. Directions within ±45 degrees of the longitudinal direction are considered to be "longitudinal".

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ±45 degrees of the lateral direction are considered to be "lateral".

The terms "machine direction" or "MD" refer to a direction which is generally parallel to the forward direction of a material, member, element, item, component, etc. through a process. For example, nonwovens are typically formed with a machine direction that corresponds to the long or rolled direction of fabrication. The machine direction can also be the primary direction of fiber orientation in the nonwoven.

The terms "cross machine direction" or "CD" refer to a direction which is generally perpendicular to and in the same plane as the machine direction.

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using a refastenable fastening system. A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

Description:

Fastening systems constructed in accordance with the present invention comprise receiving components which can reduce the pressure fluctuations which can occur when producing the receiving component. Specifically, receiving components constructed in accordance with the present invention comprise a bond pattern which can reduce the pressure fluctuations experienced by the receiving component during processing. Additionally, a receiving component constructed in accordance with the present invention can maintain a sufficient area of unbonded fibers and/or unbonded portions of bonded fibers such that the receiving component can be used with suitable engaging components in a fastening system.

As shown in FIG. 1A, a fastening system 10 constructed in accordance with the present invention may comprise an engaging component 12 and a receiving component 100. The engaging component 12 may comprise a plurality of hooks 14 which extend outward from an engaging surface 16. The receiving component 100 may comprise a plurality of looped fibers (not shown) which are capable of becoming entangled with the plurality of hooks 14 of the engaging component 12. Examples of suitable engaging components are discussed hereafter.

The fastening system 10 can be utilized in a variety of consumer and commercial goods which may benefit from having the fastening system of the present invention. Some examples of articles which can utilize the fastening system of the present invention include disposable absorbent articles, body wraps, packaging, and industrial connections for abrasive pads, medical products, and the like.

Figure 1B:
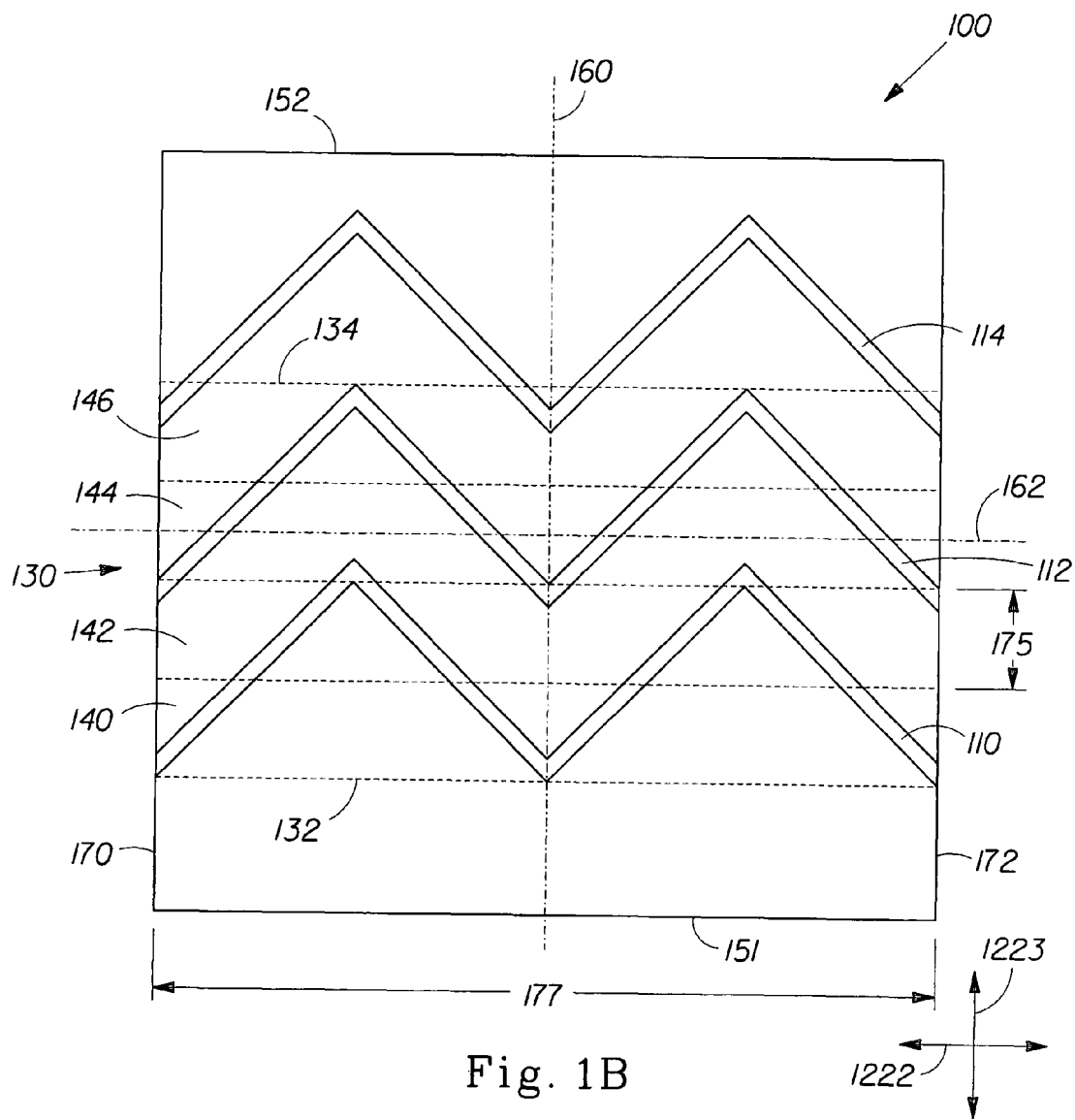
FIG. 1B is a plan view showing a receiving component of the fastening system of FIG. 1A, the receiving component being constructed in accordance with the present invention.

As shown in FIG. 1B, the receiving component 100, constructed in accordance with the present invention, may comprise a plurality of bond lines, a bond zone 130, and a plurality of consecutive sweep regions. In some embodiments, the receiving component 100 may comprise a first bond line 110, a second bond line 112, and a third bond line 114. Embodiments having more than three bond lines and less than three bond lines are contemplated.

The first bond line 110, in some embodiments, can be disposed adjacent to a first end edge 151 and the second bond line 112 can be disposed adjacent to the first bond line 110. The third bond line 114, in some embodiments, can be disposed adjacent to a second end edge 152 and adjacent the second bond line 112. In some embodiments, the first end edge 151 and the second end edge can extend from a first longitudinal edge 170 to a second longitudinal edge 172 in a direction generally parallel to a lateral axis 162.

As shown, in some embodiments, the first bond line 110, the second bond line 112, and the third bond line 114, can extend in a first direction 1222 from a first longitudinal edge 170 to a second longitudinal edge 172 of the receiving component 100. In some embodiments, the first direction 1222 can be generally parallel to the lateral axis 162. The first longitudinal edge 170 and the second longitudinal edge 172 can extend between the first end edge 151 and the second end edge 152 in a direction generally parallel to a longitudinal axis 160.

The receiving component 100 further comprises the bond zone 130. The bond zone 130 circumscribes more than one bond line. For example, as shown, the bond zone 130 can circumscribe the first bond line 110 and the second bond line 112. The bond zone 130, in some embodiments, may comprise a rectangle which contacts the outermost points of the first bond line 110 and the outermost points of the second bond line 112. In some embodiments, the outermost points of the first bond line 110 are those points on the first bond line 110 which are nearest the first end edge 151, nearest the first longitudinal edge 170, and nearest the second longitudinal edge 172. Similarly, in some embodiments, the outermost points of the second bond line 112 are those points on the second bond line 112 which are nearest the second end edge 152, the first longitudinal edge 170, and the second longitudinal edge 172. In some embodiments, the third bond line 114 can overlap into the bond zone 130 adjacent a second boundary 134 of the bond zone 130. In some embodiments, additional bond lines may overlap into the bond zone 130 either adjacent to a first boundary 132 or adjacent to the second boundary 134.

A plurality of consecutive sweep regions 140, 142, 144, and 146, can be disposed within the bond zone 130. A sweep region comprises a portion of the receiving component 100 and is used to analyze the bonded area and total area of the portion of the receiving component 100 within that sweep region. An advantage of sweep regions with smaller lengths 175 is that essentially more data points on the bond lines can be collected. The higher number of data points can increase the accuracy of the calculation of the variability in the bonded area in the receiving component 100. The cumulative lengths 175 of the sweep regions 140, 142, 144, and 146, are equal to the length of the bond zone 130.

Each sweep region 140, 142, 144, and 146, comprises a portion of the first bond line 110 and/or the second bond line 112. In some embodiments, some of the consecutive sweep regions 140, 142, 144, and 146, may comprise portions of additional bond lines which overlap into the bond zone 130 either adjacent to the first end edge 151 or the second end edge 152. For example, because the third bond line 114 overlaps the bond zone 130, the sweep region 146 may further comprise a portion of the third bond line 114.

At least one sweep region comprises a portion of both the first bond line 110 and the second bond line 112. For example, as shown, in some embodiments, two sweep regions, i.e. 142 and 144, comprise a portion of the first bond line 110 and the second bond line 112. Depending on the sizes of the sweep regions, one or more sweep regions may comprise portions of more than one bond line. Embodiments comprising more than four sweep regions and fewer than four sweep regions are contemplated.

Because the sweep regions 140, 142, 144, and 146, are consecutive, each sweep region shares a boundary with an adjacent sweep region. For example, sweep region 140 shares a boundary with sweep region 142. Similarly, sweep region 144 shares a boundary with sweep region 142. However, the sweep regions 140, 142, 144, and 146, are arranged such that the odd (first and third) sweep region, e.g. 140 and 144 do not share a boundary. Additionally, the sweep regions 140, 142, 144, and 146, are arranged such that the even (second and fourth) sweep regions, e.g. 142 and 146, do not share a boundary.

The consecutive sweep regions 140, 142, 144, and 146, are rectangular and extend from the first longitudinal edge 170 to the second longitudinal edge 172 of the receiving component 100. The consecutive sweep regions 140, 142, 144, and 146, have a width 177 which can be equal to a width of a web of fibrous material which the receiving component may comprise. The width 177 can be generally parallel to the lateral axis 162. In some embodiments, the sweep regions 140, 142, 144, and 146, can have the length 175 which is equal to a contact length 250 (shown in FIG. 2B) between calendering rolls. In some embodiments, the sweep regions 140, 142, 144, and 146, can have the length 175 which is less than the contact length 250 (shown in FIG. 2B). In some embodiments, the length 175 can range from about 0.1 mm to about 1.2 mm or any individual number within the range. The length 175 can be generally parallel to the longitudinal axis 160.

Each of the sweep regions 140, 142, 144, and 146, comprises the length 175 which is equal to the length 175 of adjacent sweep regions. Additionally, as shown, in some embodiments, the sweep region 140 may share the first boundary 132 with the bond zone 130. Also, in some embodiments, the sweep region 146 can share the second boundary 134 with the bond zone 130.

Each sweep region 140, 142, 144, and 146, comprises a bonded area which is defined by the bonding pattern. The percentage bonded area in a sweep region is a measure of the fiber-to-fiber bonds within the sweep region. Specifically, the percentage bonded area is determined by calculating the area of the fiber-to-fiber bonds within a particular sweep region, and dividing this area by the total area in the sweep region and multiplying by 100.

The bonded areas of the sweep regions 140, 142, 144, and 146, can vary. The variability of the amount of the bonded areas among the sweep regions 140, 142, 144, and 146, can be determined by comparing a value of the largest bonded area of a sweep region to a value of the lowest bonded area of another sweep region. A ratio of the largest bonded area and the lowest bonded area between any two sweep regions is termed the bond ratio. In some embodiments, the bond ratio is greater than or equal to about 1 and less than about 20 or any individual number within the range. In other embodiments, the bond ratio is greater than or equal to about 1 and less than or equal to about 10. In other embodiments, the bond ratio is greater than or equal to about 1 and less than or equal to about 3. In some embodiments, where the bond ratio is 1, there may not be a value of the largest bonded area or a value of the lowest bonded area. In this instance, the value of one bonded area can be divided by the value of another bonded area.

Adding the bonded areas of each of the individual sweep regions can provide the cumulative bonded area. Adding the total areas of each of the individual sweep regions can provide the cumulative total area. Dividing the cumulative bonded area by the cumulative total area can provide the overall bonded area of the bond zone 130, in some embodiments, or the overall bonded area of the receiving component 100 in other embodiments.

Figure 2A:
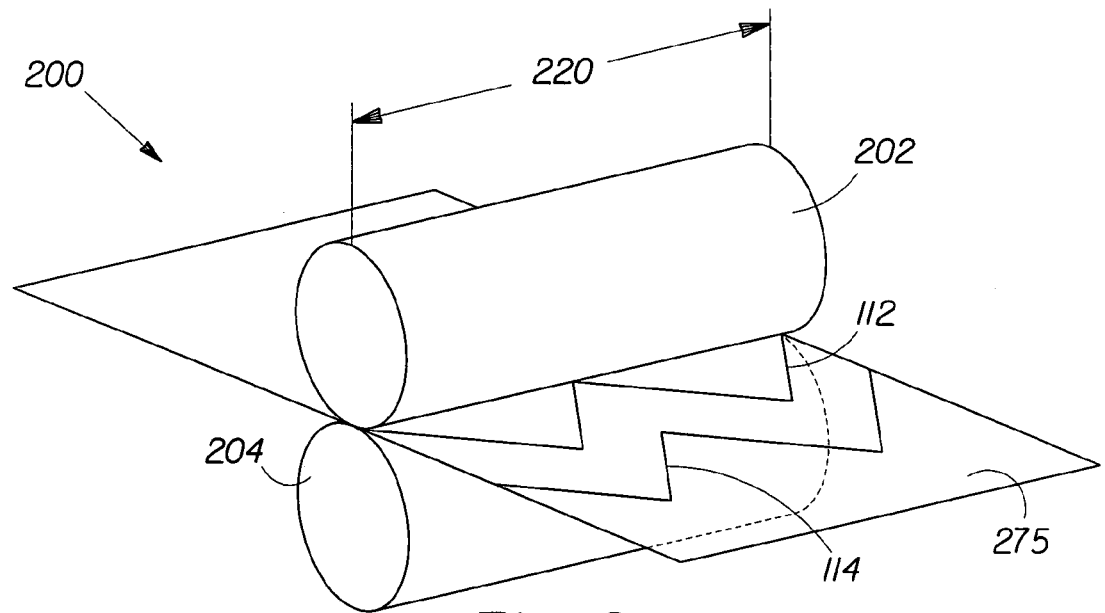
FIG. 2A is a schematic view showing a process for producing bonding patterns in accordance with the present invention.
Figure 2B:
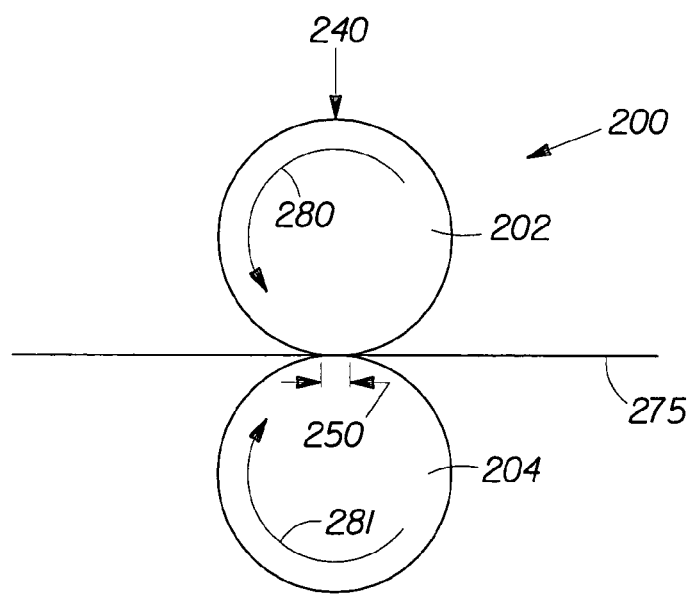
FIG. 2B is an elevation view showing a side of a pair of calendering rolls of the process of FIG. 2A.

As shown in FIGS. 2A and 2B, the bond lines, e.g. 110 (shown in FIG. 1B), 112 and 114, of a receiving component 100 (shown in FIG. 1), in some embodiments, can be produced via a calendering system 200. The calendering system 200 may comprise a pair of calendering rolls 202 and 204 which create a nip therebetween. The outer surface of the calender roll 202 and/or the calender roll 204 may comprise protrusions (not shown) extending outward from their outer surface. These protrusions typically create fiber-to-fiber bonds in a web of fibrous material 275 as the web of fibrous material 275 passes through the nip. The receiving component 100 (shown in FIGS. 1A and 1B) may comprise a portion of the web of fibrous material 275.

The web of fibrous material 275 can pass through the calendering rolls 202 and 204 in a direction generally parallel to the longitudinal axis 160 (shown in FIG. 1B) of the receiving component 100 (shown in FIGS. 1A and 1B). Specifically, the longitudinal axis 160 (shown in FIG. 1B) of the receiving component 100 (shown in FIGS. 1A and 1B) can be generally parallel to a machine direction of the calendering system 200. The calendering rolls 202 and 204 can rotate in direction shown by arrows 280 and 281 (shown in FIG. 2B), respectively.

In some embodiments, the calendering rolls 202 and/or 204 can be heated. The calendering rolls 202 and 204 can provide energy to the web of fibrous material 275 as the web of fibrous material 275 passes through the nip. Additionally, in some embodiments, a force 240 can be applied to the calendering rolls 202 and/or 204 such that a pressure is applied to the web of fibrous material 275 as it passes through the nip. The force 240 which can be applied to the calendering rolls 202 and/or 204 is discussed hereafter.

The surface to surface contact of the calendering rolls 202 and 204 can define the contact length 250. The contact length 250 is defined by a portion of the calender roll 202 and a portion of the calender roll 204 which are in contact with the web of fibrous material 275 (shown in FIG. 2A) as the web of fibrous material 275 (shown in FIG. 2A) passes through the nip. In some embodiments, the contact length 250 can be determined via the Hertzian equation below. The Hertzian equation assumes that the calendering rolls 202 and 204 are made from homogeneous, isotropic material, and further assumes the validity of Hooke's law. Other assumptions include that the calendering rolls 202 and 204 have equal diameters; that the calendering rolls 202 and 204 are created from material which has the same elastic modulus; and that the width 220 of the calendering rolls 202 and 204 are at least as wide as the width 177 (shown in FIG. 1B) of the sweep regions. The contact length 250 can be found via the following equation:

$$X = \sqrt{\frac{8FR(1-v^2)}{\pi EL}}$$

where X is ½ the width of the contact area 250;
R is the radius of the calender roll 202 or 204 in millimeters;
F is the force applied in Newtons/mm;
E is the elastic modulus of the material of the calender rolls 202 and 204;
L is the width of the calender rolls 202 and 204 (as shown 220); and
v is Poisson's ratio.

Where the calendering rolls do not have equal diameters, one skilled in the art could rederive the above equation taking into account the unequal diameters of the calendering rolls. Where the calendering rolls are not made from materials which have equal elastic moduli, one skilled in the art could rederive the above equation taking into account the unequal elastic moduli of the calendering rolls.

In some embodiments, where the calendering rolls are made of steel, the elastic modulus E can be equal to 210,000 N/mm$^2$, Poisson's ratio can be 0.3, and applied force F can be between about 30 N/mm to about 150 N/mm. As mentioned above, X is equal to ½ of the contact length 250. Thus, multiplying X by two provides the contact length 250. In some embodiments, the contact area 250 can be in a range from about 0.1 mm to about 1.2 mm or any individual number within the range. In some embodiments, the contact area 250 can be in a range from about 0.7 mm to about 1.0 mm.

One advantage of the present invention is that because of the ratio of larger bonded area to lesser bonded of the present invention, pressure fluctuations during the calendering process can be reduced. For example, in conventional receiving components where bond areas vary among sweep regions by more than 2000%, the contact area of the calendering rolls producing these bonded areas varies by more than 2000% also. Consequently, if the force applied to the calender rolls is constant, the pressure applied to a web of fibrous material as it passes through the nip of the calender rolls varies by more than 2000% as well. In conventional receiving components pressure fluctuations of greater than 2000% can occur when some sweep regions comprise a 0% bonded area, thereby yielding a ratio of larger bonded area to lesser bonded area which is infinite. The zero percent bonded area can occur, for example, when a first bond line and a second bond line are separated by a finite distance in a direction generally parallel to the longitudinal axis of the receiving component which is equal to at least the length of a sweep region. As another example, pressure fluctuations of greater than 2000% can also occur where there is too much overlap between bond lines or too little. The overlap between bond lines is discussed further with regard to FIG. 3.

From a process perspective, the pressure fluctuations of greater than 2000% can cause process instabilities. For example, the extreme pressure fluctuations can cause premature failure of the protrusions on the calender rolls.

From a product/material performance perspective pressure fluctuations of greater than 2000% are also not typically desirable. For example, a sweep region having 0% bonded area can provide low shear capability and potentially poor refastenability results. Specifically, because less loose fiber ends are bonded within this sweep region, fuzzing can result during multiple opening and closing cycles with suitable engaging components.

Also, sweep regions having 0% bonded area can reduce the strength in a direction parallel to a lateral axis of the receiving component. The lateral axis of the receiving component, in some embodiments can be associated with the direction of shear in many instances. For example, in a fastened state, the lateral axis of the receiving component can be generally parallel to the direction of shear. For example, referring to FIG. 8A momentarily, in a fastened state, shear forces can act along a primary direction of shear 775 which is generally parallel to a lateral axis of a receiving component 740. Where there is no overlap between adjacent bond lines, the receiving component material in between adjacent bond lines remains free to move with the applied shear force.

In contrast, where the overlap between bond lines causes pressure fluctuations of greater than 2000%, the concentration of fiber-to-fiber bond sites in the region of overlap will generally provide poor fastenability results. For example, as stated previously, engaging components generally are not able to engage receiving components at the bonded areas.

Additionally, the pressure fluctuations of greater than 2000% can also cause variable bonding quality, as discussed previously. When pressure fluctuations are greater than 2000%, fiber-to-fiber bonds in the lesser bonded area sweep regions experience higher pressure than larger bonded area sweep regions and can incur holes because of the higher pressure. Also, the fiber-to-fiber-bonds in the larger bonded area sweep regions can experience lower pressure than lesser bonded area sweep regions and can incur less fiber-to-fiber bonds because of the lower pressure. Specifically, the lower pressure, in some cases, can merely compress fibers instead of actually bonding them.

Figure 2C:
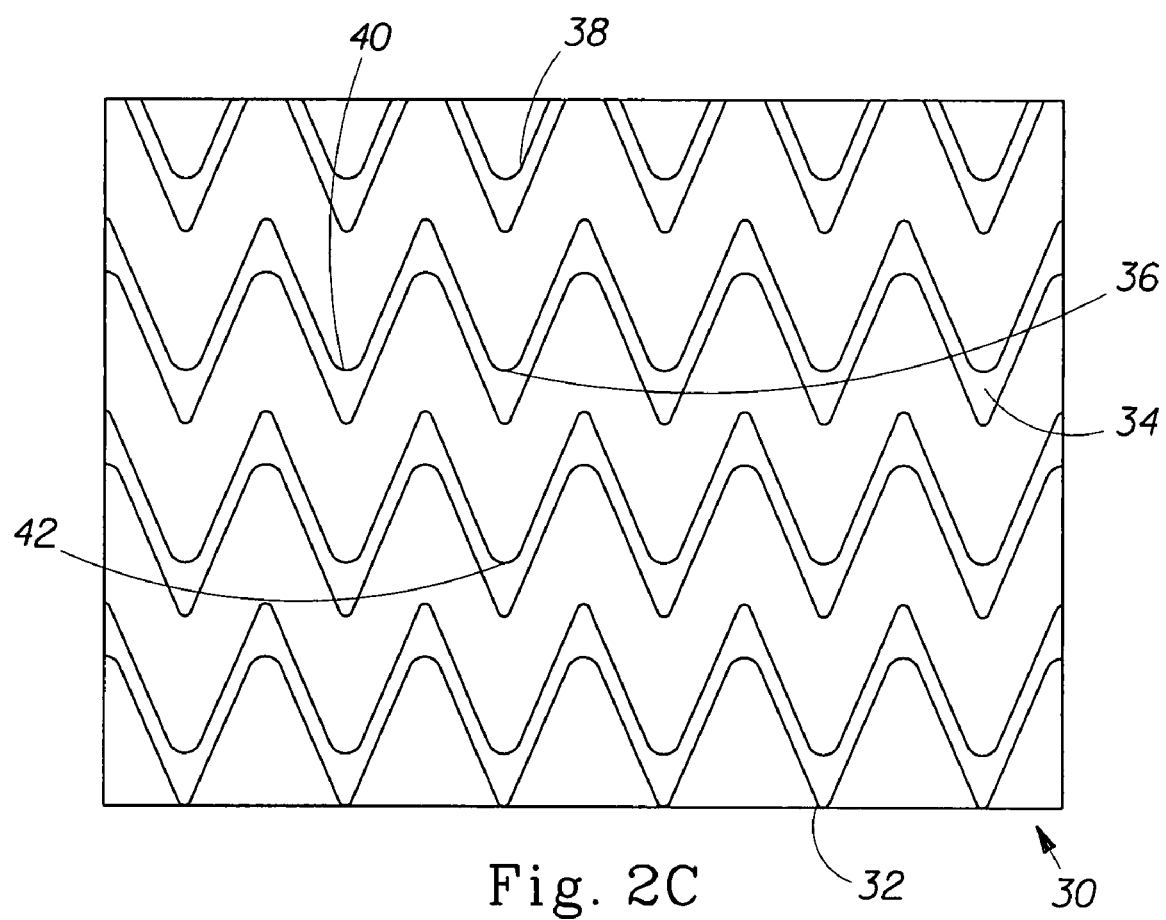
FIG. 2C is a plan view showing a receiving component constructed in accordance with the present invention.

As shown in FIG. 2C, a receiving component 30 was constructed in accordance with the present invention and incurred some defects, e.g. 32, 34, 36, 38, 40, and 42. The bond ratio in the receiving component 30 was about 1.8. It is believed that at ratios of about 20 or less, an acceptable number of defects may exist. However, for bond ratios above 20 an unacceptable amount of defects would occur in a receiving component and therefore be outside the range of the present invention.

In contrast, with conventional receiving components, a receiving component constructed in accordance with the present invention reduces pressure fluctuations below about 2000%. The reduction in pressure fluctuation, in part, is accomplished by assuring that a bond area of the receiving component comprises a plurality of sweep regions which each have some finite amount of bonded area. Additionally, the sweep regions for receiving components constructed in accordance with the present invention comprise bonded area percentages which reduce pressure fluctuations below about 2000%.

There are several factors which can impact the ratio of larger bonded area to lesser bonded area. Some factors include the overlap of the bond lines, in some embodiments, the orientation angle of the bond lines, the period of the bond lines, and in some embodiments, the orientation of the bond lines during processing. The orientation of the bond lines during processing is discussed further in regard to FIG. 6.

Figure 3:
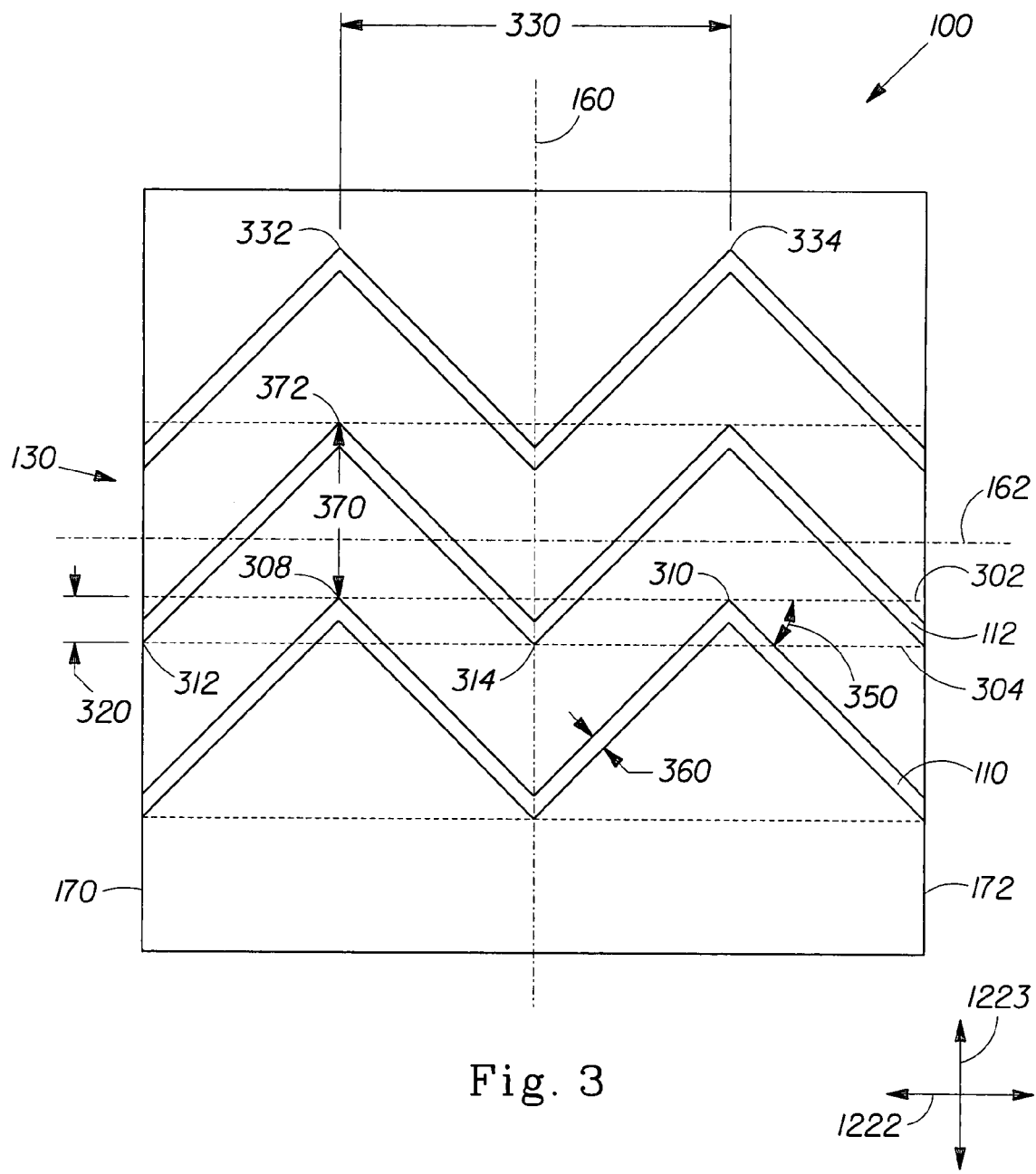
FIG. 3 is a plan view showing the receiving component of FIG. 1 highlighting additional features of the bonding pattern.

As shown in FIG. 3, the overlap 320 is a distance between a first reference line 302 and a second reference line 304. In some embodiments, the overlap 320 is generally parallel to the longitudinal axis 160 and generally parallel to a second direction 1223. The first reference line 302, in some embodiments, can be drawn between two inwardmost points 308 and 310 on the first bond line 110 and can be generally parallel to the lateral axis 162. In some embodiments, the second reference line 304 can be drawn between two inwardmost points 312 and 314 of the second bond line 112 and can be generally parallel to the lateral axis 162. In some embodiments, the inward most points 308 and 310 of the first bond line 110 can be the points nearest the second bond line 112. Similarly, in some embodiments, the inwardmost point 312 and 314 of the second bond line 112 can be the point nearest the first bond line 110. Where the first bond line 110 does not intersect the second reference line 304, and where the second bond line 112 does not intersect the first reference line 302, there is no overlap between the first bond line 110 and the second bond line 112.

Additionally, FIG. 3 shows a period 330, an orientation angle 350, bond line spacing 370, and a bond line thickness 360. In some embodiments, the period 330 can be the smallest interval after which a periodic function takes the same values. As shown, in some embodiments, the period 330 can be a distance from a first peak 332 of the third bond line 114 to a second peak 334 of the third bond line 114. In embodiments where the first bond line 110 and the second bond line 112 are similar to the third bond line 114, the period 330 can be found similarly for the first bond line 110 and the second bond line 112. An orientation angle 350, where a portion of the first bond line 110 intersects the first reference line 302, is also shown.

The bond line spacing 370 is the distance between the first and second bond lines 110 and 112. For example, in some embodiments, the bond line spacing 370 can be measured from the inwardmost point 308 of the first bond line 110 to the outward most point 372 on the second bond line 112. The outwardmost point 372 on the second bond line 112, in some embodiments, can be the point nearest the third bond line 114. In some embodiments, the bond line spacing 370 can be generally parallel to the longitudinal axis 160. Any suitable spacing can be used. For example, the spacing 370 between the bond lines can be in a range from about 1 mm to about 20 mm or any individual number within the range. As yet another example, the spacing 370 can be between about 3 mm and about 18 mm. As yet another example, the spacing 370 can be between about 6 mm and about 12 mm.

Similarly, any suitable bond line thickness 360 can be utilized. For example, in some embodiments, the bond line thickness 360 can be in a range from about 0.2 mm to about 5 mm or any individual number within the range. In some embodiments, the bond line thickness 360 can be in a range from about 0.5 mm to about 2 mm. In some embodiments, the bond line thickness 360 can be in a range from about 1 mm to about 1.5 mm.

Any suitable period 330 can be used in conjunction with the present invention. For example, in some embodiments, the period 330 can be in a range from about 1 mm to about 20 mm or any individual number within the range. In some embodiments, the period 330 can be in a range from about 1.5 mm to about 15 mm. In some embodiments, the period 330 can be in a range from about 5 mm to about 12 mm.

The effect that the overlap of the bond lines has on the ratio of larger bonded area to lesser bonded area is illustrated in Table I. Table I contains prophetic examples, and all calculations contained in Table I are based on a zigzag bond line pattern similar to the bond line pattern shown in FIG. 1.

TABLE I

| | Example # | | | | |
|---|---|---|---|---|---|
| | 1 | 2 | 3 | 4 | 5 |
| Line Thickness (mm) | 1 | 0.5 | 0.5 | 1 | 0.5 |
| orientation angle (degrees) | 63.4 | 63.4 | 63.4 | 63.4 | 63.4 |
| Period "T" (mm) | 9.3 | 9.3 | 9.3 | 9.3 | 9.3 |
| line spacing (mm) | 6 | 6 | 12 | 3 | 3 |
| Contact width (mm) | 0.25 | 0.25 | 0.25 | 0.25 | 0.25 |
| Overlap (mm) | 5.52 | 4.4 | 0 | 8.52 | 7.4 |
| Overall Area, % Bonded | 37.2 | 18.6 | 9.3 | 74.4 | 37.2 |
| Larger Area (mm^2) | 1.12 | 0.56 | 0.28 | 1.75 | 0.91 |
| Lesser Area (mm^2) | 0.56 | 0.28 | 0.00 | 1.68 | 0.84 |
| Larger/Lesser Ratio | 2.00 | 2.00 | infinite | 1.04 | 1.09 |
| Max Area, % Bonded | 48.10 | 24.05 | 12.03 | 75.23 | 39.15 |
| Min Area, % Bonded | 24.06 | 12.03 | 0.00 | 72.16 | 36.08 |
| Max/Min Ratio (%/%) | 2.00 | 2.00 | infinite | 1.04 | 1.09 |

As shown in Table I and as discussed previously (see Example 3), where the overlap of the bond lines is equal to zero, the ratio of larger bonded area to lesser bonded area can be infinite in some instances. In contrast, in the embodiments of the present invention, the first bond line 110 (shown in FIG. 1) and the second bond line 112 (shown in FIG. 1) overlap one another by a finite amount. As shown, see Example 1 and 4, as the overlap increases, the ratio of larger area to lesser area decreases.

The overlap can be impacted by the thickness of the bond lines. For example, in Table I, as the thicknesses of the bond lines decrease, the overlap between the bond lines can similarly decrease (see Example 1 and 2). Additionally, the thickness of all the bond lines in one pattern can be changed as desired to adjust the overall percent bonded area of the bond pattern. Similarly, the overlap can be impacted by the spacing of the bond lines. For example, in Table I, as the spacing between the bond lines increase, the overlap between the bond lines decreases (see Examples 1 and 4; 2 and 5).

The effect that the orientation angle 350 has on the ratio of larger bonded area to lesser bonded area is illustrated in Table II. Table II contains prophetic examples, and all calculations contained in Table II are based on a zigzag bond line pattern similar to the bond line pattern shown in FIG. 1.

TABLE II

| | EXAMPLE #: | | | | | |
|---|---|---|---|---|---|---|
| | 6 | 7 | 8 | 9 | 10 | 11 |
| Line Thickness (mm) | 1 | 1 | 1 | 1 | 1 | 1 |
| Orientation Angle (degrees) | 75 | 65 | 60 | 55 | 45 | 65.082 |
| Period (mm) | 9.3 | 9.3 | 9.3 | 9.3 | 9.3 | 9.3 |
| Line Spacing (mm) | 18.7 | 9.8 | 7.53 | 5.86 | 3.54 | 10.01 |
| Contact Length (mm) | 0.5 | 0.5 | 0.5 | 0.5 | 0.5 | 0.5 |
| Overlap (mm) | 2.52 | 2.54 | 2.52 | 2.52 | 2.52 | 2.37 |
| Lesser bonded area (%) | 14.51 | 23.73 | 24.83 | 26.25 | 30.41 | 23.71 |
| Larger bonded area (%) | 22.26 | 25.45 | 31.34 | 38.01 | 53.87 | 23.71 |
| Ratio Larger/Lesser | 1.53 | 1.07 | 1.26 | 1.45 | 1.77 | 1.00 |
| Overall Area % Bonded | 20.7 | 24.1 | 25.0 | 29.8 | 30.7 | 23.71 |

For the examples shown above, the orientation angle 350 (shown in FIG. 3) is changed for a zigzag bond pattern similar to the bond pattern shown in FIG. 1. As shown, the orientation angle 350 (shown in FIG. 3) was manipulated from about 75 degrees to about 45 degrees, while maintaining an overlap of about 2.5 mm for most examples. In order to ensure an equal amount of overlap for most examples, the line spacing was also varied for each orientation angle 350 (shown in FIG. 3). In some examples, the period and the bond line thickness were kept constant.

In example 6, the orientation angle is at 75 degrees, resulting in the lowest overall percentage bonded area of 20.7% compared to the other examples in Table II. Without wishing to be bound by theory, it is believed that as the overlap remains constant at about 2.5 mm, this low percentage bond area is the consequence of the line spacing of 18.7 mm, the line thickness of 1 mm, and the period of 9.3 mm.

As shown in example 7, at an orientation angle of 65 degrees, while maintaining the overlap at 2.5 mm, the total percentage of bonded area can increase to 24.1% at a line spacing of 9.8 mm. The reduction in the orientation angle by about 10 degrees from example 6 can reduce the ratio of larger bonded area to lesser bonded area from 1.53 to 1.07.

In accordance with the present invention, the orientation angle 350, in some embodiments, can range from about 45 degrees to about 75 degrees or any individual number within the range. In other embodiments, the orientation angle 350 can range from about 55 degrees to about 65 degrees. In yet other embodiments, the orientation angle 350 can range from about 60 to about 65 degrees.

Example 11, illustrates, in one particular embodiment, how the ratio of larger to lesser bonded area can be made to equal 1.0 for a zigzag bond line pattern similar to that shown in FIG. 1. In some embodiments, the ratio of larger to lesser bonded area can be equal to about 1.0 by adjusting the bond line thickness in the areas where the bond lines do not overlap. Based on the parameters and the relationships of those parameters discussed herein, the modification of at least one of the parameters and/or a relationship between parameters to achieve the ratio of larger bonded area to lesser bonded area of about 1.0 is contemplated.

The effect that the period has on the ratio of larger bonded area to lesser bonded area is illustrated in Table II. Table III contains prophetic examples, and all calculations contained in Table III are based on a zigzag bond line pattern similar to the bond line pattern shown in FIG. 1.

TABLE III

| | Example # | | | | | | | | |
|---|---|---|---|---|---|---|---|---|---|
| | 12 | 13 | 14 | 15 | 16 | 17 | 18 | 19 | 20 |
| Line Thickness (mm) | 1 | 1 | 1 | 1 | 1 | 1 | 1 | 1 | 1 |
| Orientation angle (degrees) | 60 | 60 | 60 | 60 | 60 | 60 | 60 | 60 | 60 |
| Period (mm) | 5 | 6 | 7 | 8 | 9 | 8 | 9 | 10 | 11 |
| Line Spacing (mm) | 6.2 | 6.2 | 6.2 | 6.2 | 6.2 | 7 | 7.9 | 8.7 | 9.6 |
| Contact Length (mm) | 0.5 | 0.5 | 0.5 | 0.5 | 0.5 | 0.5 | 0.5 | 0.5 | 0.5 |
| Amplitude | 3.17 | 3.6 | 4.03 | 4.46 | 4.90 | 4.46 | 4.9 | 5.33 | 5.76 |
| Overlap (mm) | 0.13 | 1.00 | 1.86 | 2.73 | 3.59 | 1.93 | 1.89 | 1.96 | 1.93 |
| Lesser Area Bonded (%) | 6.16 | 19.17 | 30.72 | 28.87 | 25.66 | 27.83 | 24.30 | 22.63 | 20.22 |
| Larger Area Bonded (%) | 46.19 | 38.49 | 32.99 | 39.38 | 46.00 | 28.87 | 25.66 | 23.09 | 20.99 |
| Ratio larger/lesser Area Bonded | 7.50 | 2.01 | 1.07 | 1.36 | 1.79 | 1.04 | 1.06 | 1.02 | 1.04 |
| Overall Area Bonded (%) | 32.3 | 32.3 | 32.3 | 32.3 | 32.3 | 28.6 | 25.3 | 23.0 | 20.8 |

At an equal percentage of the total bonded area, the determined larger bonded area to lesser bonded area ratio is at 1.07 for a period equal to about 7. The overlap for example 13 can be about 1.9 mm. Based on the data in Table III, in some embodiments, the period can range from about 5 mm to about 11 mm or any number within the range. In other embodiments, the period can range from about 6 mm to about 8 mm. In yet other embodiments, the period can be about 7 mm.

As shown in examples 17-20, the bond line spacing can be adjusted such that overall bonded area is impacted. In some embodiments of the present invention, the overall bonded area can be in a range from about 10% to about 50% or any individual number within the range. In other embodiments, the overall percentage of bonded area can be between about 20% to about 30%. In yet other embodiments, the overall percentage of bonded area can be between about 20% to about 25%. In other embodiments, the overall bonded area can be less than about 40% while the bonded area in any sweep region is less than about 60%. In other embodiments, the overall bonded area can be less than about 30% while the bonded area in any sweep region can be less than about 50%. In yet other embodiments, the overall bonded area can be between about 20% to about 30% while the bonded area in any sweep region is less than about 40%.

As stated previously, the data in Tables I, II, and III, are based on a zigzag bond line patterns similar to the bond line pattern shown in FIG. 1. However, one skilled in the art can calculate the values for the listed parameters in Tables I, II, and III, for any given bond line pattern or variations thereof. For example, for simple geometries, e.g. consisting of angled and connected straight lines, the values shown in Tables I, II, and III, can be calculated using the geometric and trigonometric relationships of the angled and connected straight lines as done for the bond line patterns shown heretofore. For more complex patterns, for example, those shown in FIGS. 4A-4C, or bond line patterns including shapes such as those of FIGS. 5B-5E, the values of Tables I, II, and III, can be obtained by utilizing computerized image analysis.

In computerized image analysis, the bond pattern in question is digitized such that a color contrast can be reliably measured to determine where bonded and unbonded areas are. For example, unbonded areas may be represented as white pixels and bonded areas may be represented as black pixels. The number of pixels representing a bonded area can be counted and compared to number of pixels representing an unbonded area to determine the percentage of bonded area.

Similarly, the period, overlap, bond line thickness, orientation angle, and line spacing can also be measured using computerized image analysis.

Additionally, any data or trends discussed in regard to Tables I, II, and III, are pertinent to the bond line patterns analyzed, e.g. zigzag pattern. Consequently, any data and/or trends discussed regarding Tables I, II, and III, may not be valid for other bond line patterns.

Figure 4A:
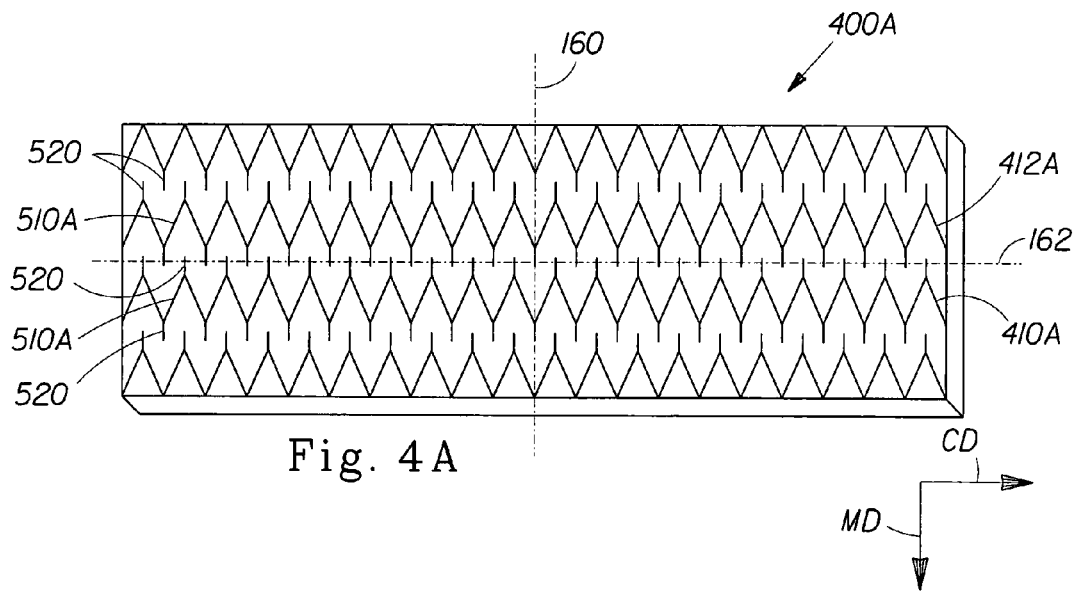
FIGS. 4A and 4B are plan views showing other embodiments of receiving components having bond patterns which are in accordance with the present invention.
Figure 4B:
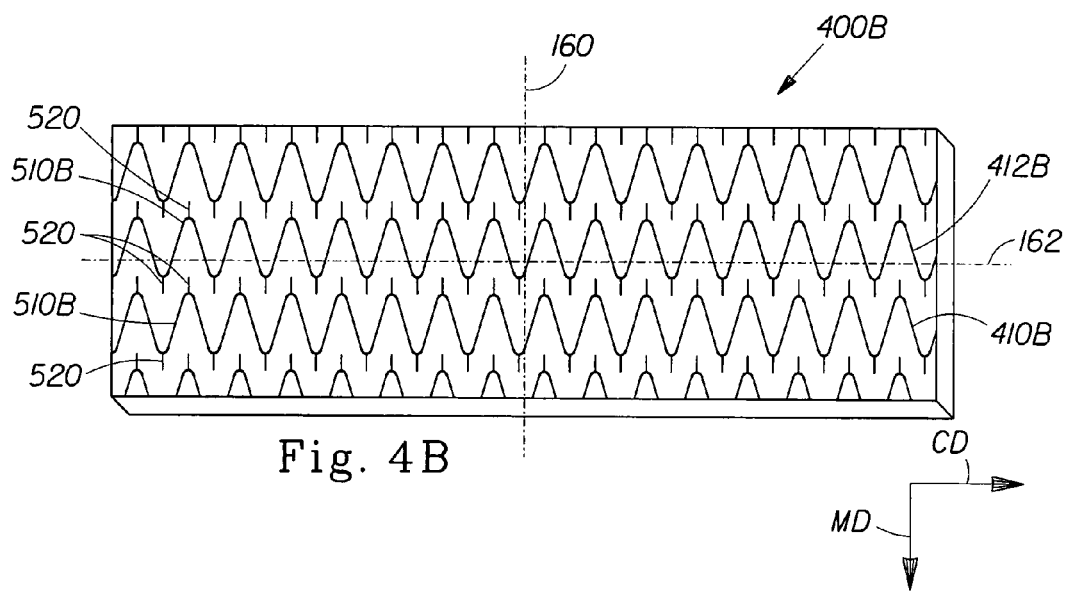
Figure 4C:
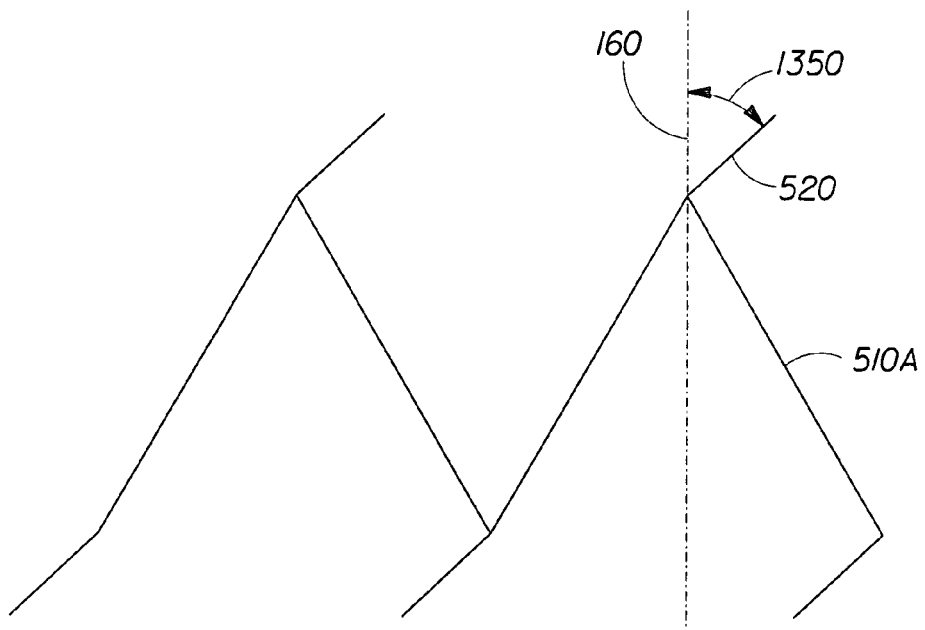
FIG. 4C is a close up view showing a section of the web of fibrous material of FIG. 4A.

As shown in FIGS. 4A-4C, the overlap between adjacent bond lines can be achieved in a number of different manners. For example, as shown in FIG. 4A, a receiving component 400A constructed in accordance with the present invention may comprise a first bond line 410A and a second bond line 412A. The first bond line 410A and the second bond line 412A may each comprise a plurality of repeating units 510A. The repeating units 510A of the first bond line 410A and the second bond line 412A, in some embodiments, can overlap one another via extensions 520 generally extending in a direction parallel to the longitudinal axis 160 from each repeating unit 510A. Also, as shown, in some embodiments, the first and the second bond lines 410A and 412B may comprise extensions 520 which extend in a direction generally parallel to the longitudinal axis 160 in between repeating units 510A.

In some embodiments, the extensions 520 may extend at an angle with respect to the longitudinal axis 160. In some embodiments, the extension angle 1350 (shown in FIG. 4C) can be in a range from greater than about 0 degrees to less than about 180 degrees or any individual number within the range. In yet other embodiments, the extension angle 1350 (shown in FIG. 4C) can be in a range of about 30 degrees and less than or equal to about 150 degrees. In yet other embodiments, the extension angle 1350 can be in a range from about 60 degrees to about 120 degrees. In some embodiments, the extension angle 1350 of all bond lines can be similar. In some embodiments, the extension angle 1350 can vary between the bond lines of a bond pattern. Additionally, in some embodiments, the extension angle 1350 can vary among repeating units 510A.

In other embodiments, as shown in FIG. 4B, a receiving component 400B constructed in accordance with the present invention may comprise a first bond line 410B and a second bond line 412B. Similarly, the first bond line 410B and the second bond line 412B may comprise a plurality of repeating units 510B having extensions 520. The extensions 520 of the repeating units 510B can be configured similarly to the extensions 520 of the repeating units 510A. Additionally, as shown in FIG. 4B, the bond lines of the present invention are not limited to rectilinear repeating units 510A. For example, as shown, in some embodiments, the bond lines may comprise a plurality of repeating units 510B comprising curvilinear segments. As shown, the repeating units 510B appear sinusoidal in nature. Examples of other repeating units are shown in FIGS. 5A-5E.

The extensions 520 of FIGS. 4A and 4B, in some embodiments, can be straight lines as shown. However, the extensions may comprise any suitable shape. For example, in some embodiments, the extensions 520 may comprise rectangles, circles, triangles, rhomboid like structures, trapezoidal like structures, any suitable polygonal shape, curvilinear lines, angled lines, squiggly lines, combinations thereof, or the like. In other embodiments, the extensions 520 may comprise aesthetic designs such as, for example, a graphic or child graphic. The graphic may be any suitable visual image or images. The graphic may include pictorial symbols and/or images, such as, but not limited to, photographs, drawings, embossments, or any other suitable materials utilized to create pictorial symbols and/or images. The pictorial symbols and/or images may include an image of a child, an anthropomorphic image of an animal or object, images of cartoons including well known cartoon characters, images of well known brand logos or the like, and/or images characters specifically created to be associated with the implement of commerce, symbols, such as, but not limited to arrows, indications or motion or movement, and the like, and combinations thereof Graphics and child graphics are discussed in U.S. Patent Publication No. 2005/0129743A1, U.S. Patent Publication No. 2005/0125923A1, and U.S. Patent Publication No. 2005/0125877A1.

Figure 4D:
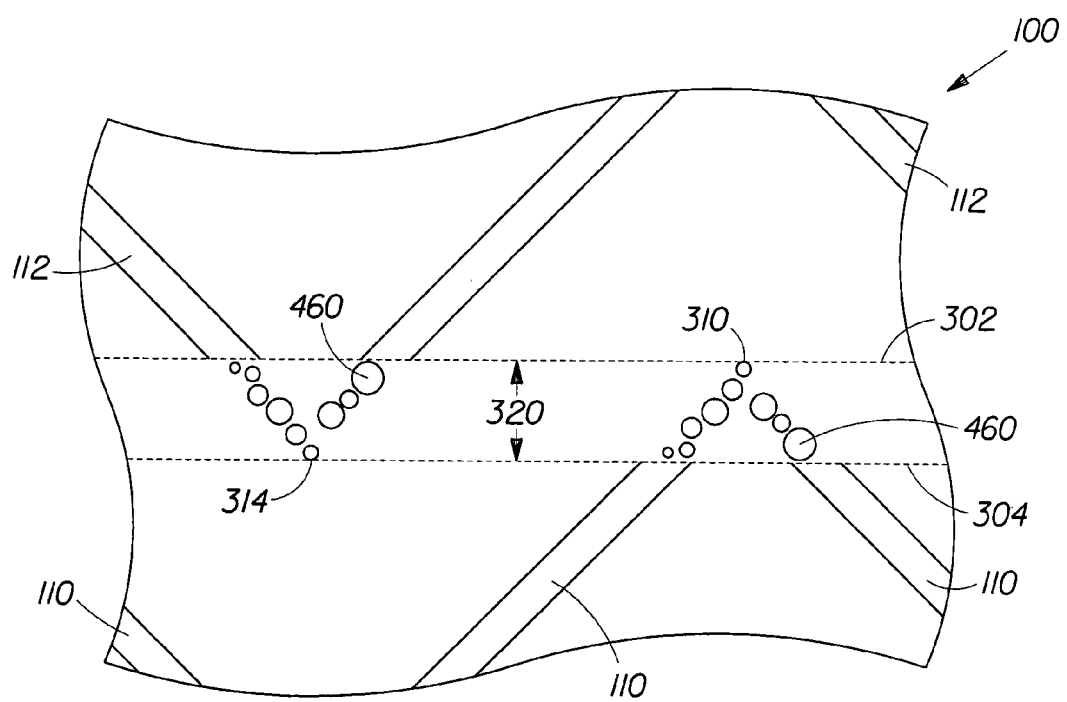
FIG. 4D is a close up view of showing a section of the receiving component of FIG. 1.

It has been found that in some embodiments, sweep regions which comprise portions of more than one bond line can have higher bonded areas than sweep regions comprising a portion of a single bond line. The bonded area of the sweep regions comprising portions of more than one bond line can be reduced by any suitable means. For example, as shown in FIG. 4D, the first bond line 110 and/or the second bond line 112 may comprise a plurality of bond sites 460 which, in some embodiments, can approximate a line. The plurality of bond sites 460 can be disposed in the overlap 320 of the first bond line 110 and the second bond line 112. In some embodiments, the plurality of bond sites 460 within the overlap 320 can define less bonded area than a continuous bond line in the overlap, thereby reducing the amount of bonded area in the overlap 320. The plurality of bond sites 460 may comprise any suitable shape known in the art.

Figure 5A:
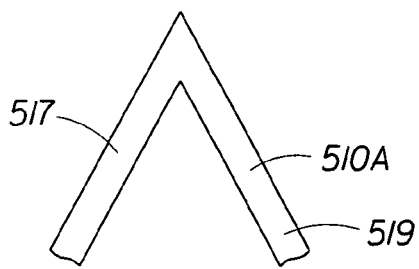
FIGS. 5A-5E are plan views showing repeating units various embodiments for repeating units which can be included in a bond pattern constructed in accordance with the present invention.
Figure 5B:
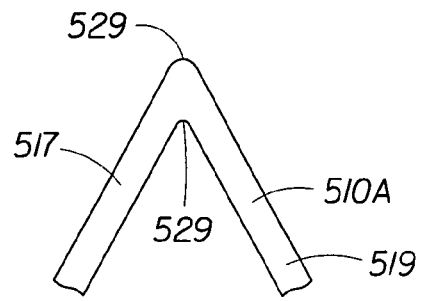
Figure 5C:
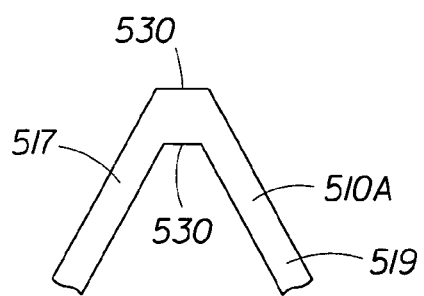

As shown in FIG. 5A, a receiving component constructed in accordance with the present invention may comprise a bond line which includes a plurality of repeating units 510A. The repeating unit 510A, in some embodiments, may comprise an open geometrical shape comprising rectilinear lines which form a first leg 517 and a second leg 519 of the repeating unit 510A. As shown in FIG. 5B, in some embodiments, the repeating unit 510A may comprise rounded edges 529 which join the first leg 517 and the second leg 519 of the repeating unit 510A. The rounded edges 529 can similarly be disposed between adjacent repeating units. As shown in FIG. 5C, the repeating unit 510A may comprise flat edges 530 which join the first leg 517 to the second leg 519 of the repeating unit 510A. The flat edges 530 can similarly be disposed between adjacent repeating units.

Figure 5D:
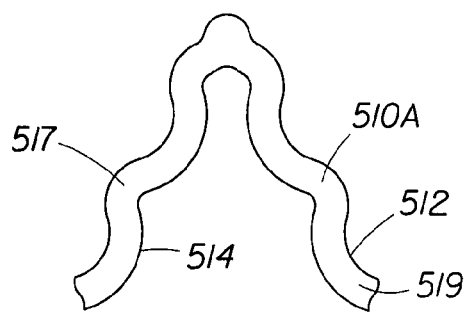
Figure 5E:
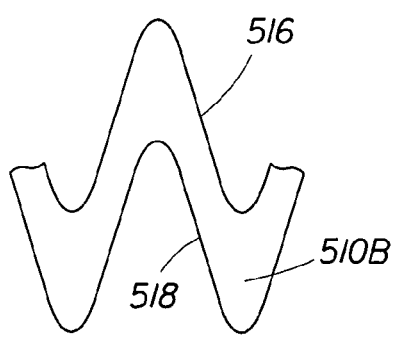

As shown in FIG. 5D, the repeating unit 510A may comprise a plurality of wavy edges 512 and 514 which define the boundary for the first leg 517 and the second leg 519. In embodiments where the bond lines comprise a plurality of repeating units having wavy edges, the bond line thickness can be determined by measuring the thickness of the repeating unit 510A in at least 10 locations and determining the average thickness therefrom. Additionally, as shown in FIG. 5E, in some embodiments, the repeating unit 510B may comprise a plurality of sinusoidal shaped edges 516 and 518.

The repeating units 510A and 510B of the present invention may comprise any suitable shape or a combination of shapes. In some embodiments, a bond line of the present invention may comprise different repeating units within the bond line. In other embodiments, the repeating units in a first bond line may be similar while a second bond line comprises a repeating unit which is different from the repeating units of the first bond line.

As mentioned previously, the orientation of the bond lines during processing can also impact the ratio of larger bonded area to lesser bonded area. In a receiving component constructed in accordance with the present invention, a longitudinal axis of the receiving component can be generally parallel to a machine direction during processing. In some embodiments, the resulting bond lines can extend from the first longitudinal edge 170 (shown in FIGS. 1B and 3) to a second longitudinal edge 172 (shown in FIGS. 1B and 3).

Figure 6:
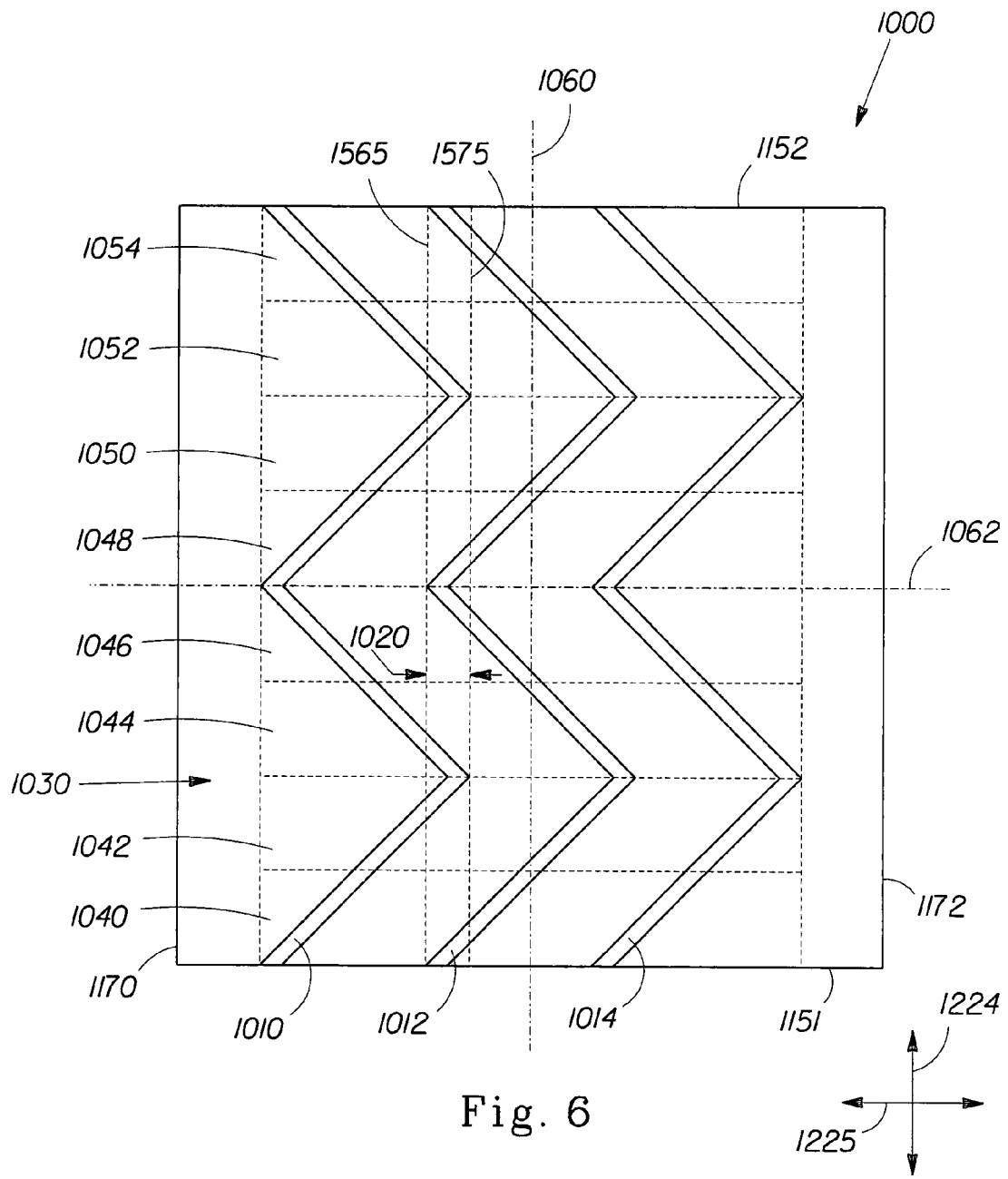
FIG. 6 is a plan view showing another embodiment of a receiving component constructed in accordance with the present invention.

In contrast, as shown in FIG. 6, in some embodiments, a receiving component 1000 constructed in accordance with the present invention may comprise a first bond line 1010, a second bond line 1012, and a third bond line 1014. In some embodiments, each of the first bond line 1010, the second bond line 1012, and the third bond line 1014, can extend from a first end edge 1151 to a second end edge 1152 of the receiving component 1000 in a first direction 1224 which is generally parallel to a longitudinal axis 1060. The receiving component 1000 may comprise a bond zone 1030 which circumscribes a bond line nearest a first longitudinal edge 1170 and a bond line nearest a second longitudinal edge 1172 and any bond lines in between. For example, as shown, the bond zone 1030 can circumscribe the first bond lines 1010, the second bond line 1012, and the third bond line 1014. Embodiments are contemplated where the receiving component comprises more than three bond lines and fewer than three bond lines.

The bond zone 1030 comprises a plurality of sweep regions 1040, 1042, 1044, 1046, 1048, 1050, and 1052. The plurality of sweep regions 1040, 1042, 1044, 1046, 1048, 1050, and 1052, may comprise similar lengths and widths to the sweep regions discussed heretofore. As shown, in some embodiments, each sweep region of the plurality of sweep regions 1040, 1042, 1044, 1046, 1048, 1050, and 1052, may comprise a portion of the first bond line 1010, a portion of the second bond line 1012, and a portion of the third bond line 1014.

Similar to the bond line pattern shown in FIG. 1B, in the bond line pattern of FIG. 6, each sweep region has some finite amount of bonded area. The first bond line 1010 can overlap the second bond line 1012, and the second bond line 1012 can overlap the third bond line 1014. However, in contrast to the overlap 320 (shown in FIG. 3) of the receiving component 100 (shown in FIGS. 1 and 3) the overlap 1020 of the receiving component 1000 can be generally parallel to the lateral axis 1062. Similarly, the second bond line 1012 can overlap the third bond line 1014.

The overlap 1020 can be the distance between a third reference line 1565 and a fourth reference line 1575. In some embodiments, the overlap 1020 can be generally parallel to a second direction 1225. The third reference line 1565, in some embodiments, can be generally parallel to longitudinal axis 1060. Similarly, the fourth reference line 1575, in some embodiments, can be generally parallel to the longitudinal axis 1060. The third reference line 1565 can extend from the first end edge 1151 to the second end edge 1152 and can intersect the inwardmost points of the first bond line 1010. The inwardmost points of the first bond line 1010 are those points which are nearest the second bond line 1012. The fourth reference line 1575 can extend from the first end edge 1151 to the second end edge 1152 and can intersect the outwardmost points of the second bond line 1012. The outwardmost points of the second bond line 1012, when referencing the overlap 1020 between the first bond line 1010 and the second bond line 1012, are those points on the second bond line 1012 which are nearest the first bond line 1010.

A receiving component of the present invention may be configured in a number of different manners. For example, in some embodiments, the receiving component may comprise a web of fibrous material such as a woven web, nonwoven web, or any combination thereof. In some embodiments, the process described in regard to FIGS. 2A and 2B can be utilized to create fiber-to-fiber bonds among loose fibers of a nonwoven, thereby creating a nonwoven web. In other embodiments, the process can be utilized to provide supplemental bonding to an already lightly bonded nonwoven web. Additionally, in some embodiments, the supplemental bonding can join the nonwoven web to a support structure. For example, the nonwoven web can have an initial bonded area of between about 10% and about 20% and can subsequently be bonded to a support layer using the bond patterns of the present invention. The resulting receiving component can have a bonded area higher than the initial bonded area.

The support layer may comprise any suitable support layer known in the art. For example, the support layer can include films or nonwoven webs. Embodiments are contemplated where the receiving component is joined to a disposable absorbent article utilizing the bond patterns of the present invention. For example, the receiving component can be joined to a backsheet of a disposable diaper.

One advantage of joining a receiving component to an underlying support layer utilizing the bond patterns of the present invention is that, in some embodiments, no adhesive is required. For example, in certain embodiments, when using a calendering system as described in regard to FIGS. 2A and 2B, the bond pattern of the present invention can be utilized to join a receiving component and a support layer without adhesive.

In certain embodiments, the initial bonded area of a receiving component may not be able to be measured. Specifically, in embodiments where the receiving component comprises a nonwoven web having hydroentangled fibers or needle punched fibers, an initial bonded area may not be ascertainable. However, these nonwoven webs can still be utilized in a receiving component and can be joined to underlying support layers using the bonding patterns of the present invention.

As mentioned previously, a receiving component constructed in accordance with the present invention may comprise a nonwoven web. In some embodiments, the nonwoven web may comprise one layer of fibers. In other embodiments, the nonwoven web may comprise more than one layer of fibers. Any suitable nonwoven web can be used. For example, a suitable nonwoven may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown meltblown spunbond (SMMS), carded, meltblown, and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded mechanically, including fibers that are needle punched or hydro entangled. Other suitable bonding processes for producing a suitable nonwoven for use in the present invention are spun bonding, thermally bonding, bonding by various types of chemical bonding such as latex bonding, powder bonding, and the like.

In certain embodiments, the basis weight of the nonwoven can be in the range of about 10 gsm to about 100 gsm or any individual number within the range. In other embodiments, the basis weight of the nonwoven can be in a range of about 25 gsm to about 80 gsm. In yet other embodiments, the basis weight of the nonwoven can be in a range of about 30 gsm to about 50 gsm.

The fibers may be of any suitable size and shape. Some examples of suitable cross sectional shapes include circular, elliptical (with or without lobe like extensions), rectangular, triangular, rhomboidal, trapezoidal, any polygon, or the like. Additionally, the cross sectional shape, in some embodiments, may include a plurality of lobes. For example, a cross sectional shape may include three lobes, i.e. trilobal. Embodiments having more than three lobes and fewer than three lobes are contemplated. In some embodiments, the fibers can be hollow. For example, the fibers may be hollow crimped fibers.

The fiber may be of any suitable denier. For example, in some embodiments, the fiber may have a denier ranging from about 1 to about 10 or any individual number within the range. In some embodiments, the denier of the fibers can range from about 1 to about 8. In other embodiments, the denier of the fibers can range from about 1 to about 5. Additionally, in some embodiments, nonwovens of the present invention can comprise fibers made of polypropylene, polyethylene, polyolefins, bicomponent fibers, or any combination thereof.

Figure 9A:
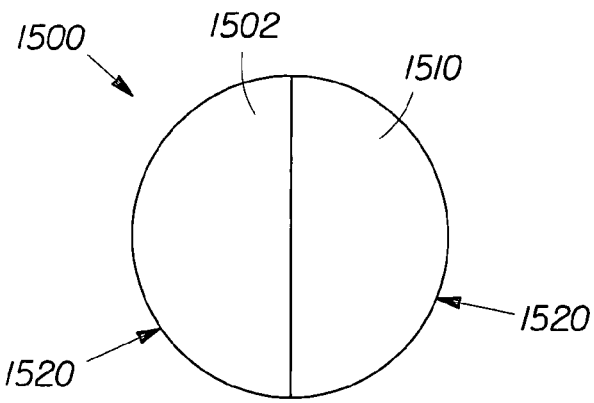
FIGS. 9A-9C show a variety of composite fibers.

Additionally, crimped composite fiber (hereinafter simply referred to as composite fiber or a nonwoven fabric laminate made with same) can be used in accordance with the present invention. The crimped composite fiber may comprise a first propylene type polymer and a second propylene type polymer. The first and second propylene type polymers can be arranged to occupy substantially separate areas at the cross sections of the composite fibers and extend continuously in the length direction. In some embodiments, each of the first and second propylene type polymers form at least a part of the peripheral surface along the length direction of the composite fiber. In some embodiments, as shown in FIG. 9A, a composite fiber 1500 can be a side-by-side type composite fiber where a first propylene type polymer 1502 and a second propylene type polymer 1510 extend side-by-side in the length direction of the composite fiber such that the first and the second propylene type polymers 1502 and 1510 each form about 50% of a peripheral surface 1520 of the composite fiber 1500.

Figure 9B:
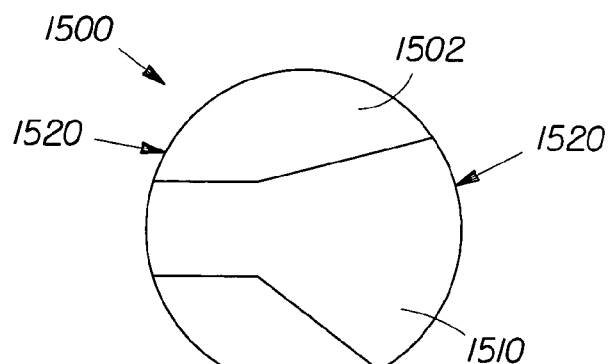
Figure 9C:
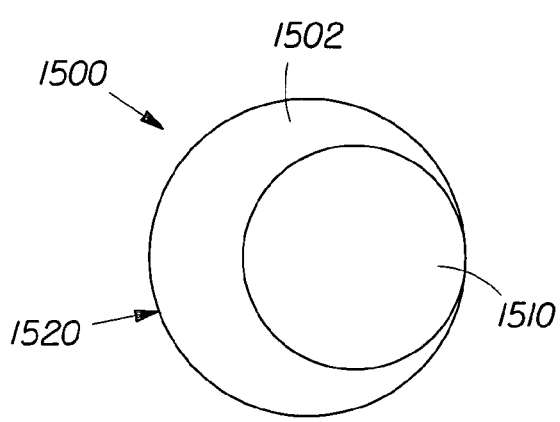

The first propylene type polymer 1502 and the second propylene type polymer 1510 can be arranged in any suitable configuration which would yield a crimp in the resulting fiber 1500. For example, in some embodiments, as shown in FIG. 9B, the second propylene type polymer 1510 may form a cross like pattern within the first propylene type polymer 1502 which is asymmetrically distributed within the first propylene type polymer. In some embodiments, as shown in FIG. 9C, the second propylene type polymer 1510 can be completely surrounded by the first propylene type polymer 1502 such that the first propylene polymer 1502 comprises about 100% of the peripheral surface 1520 of the composite fiber 1500. The second propylene type polymer 1510 can be distributed within the first propylene type polymer 1502 asymmetrically such that a crimp results in the resulting fiber 1500. In some embodiments, the first propylene type polymer 1502 and the second propylene type polymer 1510 may be in a side-by side orientation such that an opening 1530 is formed between the first propylene type polymer and the second propylene type polymer. This configuration can be similar to a hollow fiber.

Additionally, embodiments are contemplated where the second propylene type polymer 1510 comprises any number greater than about 50% of the peripheral surface 1520 of the composite fiber 1500. Additionally, embodiments are contemplated where the second propylene type polymer 1510 comprises any number less than about 50% of the peripheral surface 1520 of the composite fiber 1500. Also, the first propylene type polymer 1502 can be configured similarly to the second propylene type polymer 1510 and vice versa. Embodiments are contemplated where fibers are crimped such that they curl or form helical structures.

In some embodiments, the melting point of the first propylene type polymer 1502 measured by differential scanning calorimetry (DSC) can be at least 15° C. higher than the melting point of the second propylene type polymer 1510. In some embodiments, the melting point of the first propylene type polymer 1502 can be in a range of about 15 degrees C. to about 60 degrees C., or any number within the range, higher than the melting point of the second propylene type polymer 1510.

Furthermore, the measured weight ratio of the first propylene type polymer 1502 to the second propylene type polymer 1510 can be, in some embodiments, in the range of about 50/50 to about 5/95 or any ratio within the range. In some embodiments, the weight ratio can be in the range of about 40/60 to about 10/90 or any ratio within the range. In some embodiments, the weight ratio can be in the range of about 30/70 to about 10/90 or any ratio within the range.

In some embodiments, a possible method for determining the weight ratio of the first propylene type polymer 1502 to the second propylene type polymer 1510 may be Temperature Rising Elution Fractionation (TREF). For example, using a Cross Fractionation Chromatograph T-150A manufactured by Mitsubishi Chemicals Corporation; an IR spectrometer 1 ACVF 3.42 micrometer at 135 degrees C., manufactured by Miran; and a TREF column having an inner diameter of 4 mm and a length of 150 mm, the weight ratios may be determined.

Other steps may include, utilizing an eluent of o-dichlorobenzene (ODCB) at a flow rate of 1.0 mL/min, a concentration of sample of 30 mg/10 mL-ODCB, and a sample volume of 500 micro liters. Yet other conditions may include cooling the sample from 135 degrees C. to 0 degrees C. in 135 minutes and then holding the sample at 0 degrees C. for 60 minutes. Fractionation steps may include 0, 20, 40, 50, 60, 75, 80, 83, 86, 89, 92, 95, 98, 101, 104, 106, 108, 110, 112, 114, 116, 118, 120, 122, 125, 130, and 135 degrees C.

A resulting elution curve can be divided by a perpendicular line (perpendicular to the x-axis) at a valley between two peaks. The perpendicular line can create a first portion and a second portion of the elution curve. The first portion may comprise the area under the curve to the right of the perpendicular line while the second portion may comprise the area under the curve to the left of the perpendicular line. The weight ratio of the first propylene type polymer relative to the second propylene type polymer may be calculated by a ratio first portion to the second portion.

In some embodiments, the melt-flow rate of the first and second propylene type polymers measured according to the specification of ASTM D1238 (MFR: measuring temperature 230° C., load 2.16 kg) (second propylene type polymer/first propylene type polymer) can be in the range of about 0.8 to about 1.2 or any individual number within the range. In some embodiments, the melt-flow rate can be in the range of about 0.9 to about 1.1.

In some embodiments, the area ratio of the first propylene type polymer and the second propylene type polymer at the cross section of the composite fiber can be about the same as the weight ratio. For example, in some embodiments, a ratio of the cross sectional area of the first propylene type polymer to the cross sectional area of the second propylene type polymer can be in a range of about 50/50 to about 5/95 or any ratio within the range. In some embodiments, the ratio can be in the range of about 40/60 to about 10/90 or any ratio within the range. In some embodiments, the ratio can be in the range of about 30/70 to about 10/90 or any ratio within the range.

When the aforementioned condition is satisfied, a crimped state can be achieved in the composite fiber. A suitable number of crimps according to the specification of JIS L1015 can be in the range of about 5 crimps to about 50 crimps/25 mm or any individual number within the range.

In the present invention, measurement of the melting point of the first and second propylene type polymers based on DSC was done by an instrument of the Perkin Elmer Corp. As the sample was set on a measuring plate, the temperature was increased from 30° C. to 200° C. at a temperature increase rate of 10° C./min; 200° C. was retained for 10 min; then, the temperature was reduced to 30° C. at a temperature decrease rate of 10° C./min; then, the temperature was again increased from 30° C. to 200° C. at a temperature increase rate of 10° C./min and measurements were made on the second run.

Furthermore, it is desirable when two or more melting point peaks in the composite fiber exist based on DSC and the area of the lowest melting point peak is greater than the area of the higher melting point peak. The measurement of the melting point of the composite fiber based on DSC was done by the aforementioned device with the sample set on the measuring plate as the temperature was increased from 30° C. to 200° C. at a temperature increase rate of 10° C./min, and the aforementioned measurement was made during the first run. In the aforementioned measurement method, the melting point is obtained as the peak on the endothermic curve and the area of the melting point peak can be obtained along with the value of the melting point. When two melting point peaks of the composite fiber obtained by the measuring method of the first run overlap, the peak with an absence of other peaks is estimated according to the shape of the peak with maximum strength, and the area is obtained and comparison is made with the area of the other peaks.

In regard to the first and second propylene type polymer comprising the composite fiber of the present invention, propylene homopolymer and copolymers of propylene and one or more different types of α-olefins with 2-20 carbon atoms, preferably, 2-8 carbon atoms such as ethylene, 1-butene, 1-pentene, 1-hexene, 1-octene and 4-methyl-1-pentene, and having propylene as the primary structural unit can be utilized in some embodiments. Among those listed above, a propylene homopolymer or propylene-ethylene random copolymer having an ethylene unit content in the range of about 0 to about 10 mol % and MFR in the range of about 20 to about 200 g/10 min is desirable.

In some embodiments, the first propylene type polymer can be a propylene homopolymer and the second propylene type polymer can be a random copolymer of propylene and a small amount of ethylene having a uniform ethylene component content in the range of about 10 mol % or below, and preferably in the range of about 2 to about 10 mol %, from the standpoint of production of a nonwoven fabric having excellent fastening strength and mechanical strength as well as high bulkiness and softness suitable for use as the female component of a fastening system. In this case, the amount of ethylene unit component is obtained according to a standard method using $^3$C-NMR spectral analysis.

In some embodiments, the melting point of the first propylene type polymer can be in the range of about 120 to about 175° C., or any individual number within the range. In some embodiments, the melting point of the second propylene type polymer can be in the range of about 110 to about 155° C. The aforementioned propylene type polymers can be produced utilizing a high stereospecific polymeric catalyst.

In addition to propylene type polymers, an appropriate amount of other components may be included in the aforementioned composite fiber, as needed, as long as the purpose of the present invention is not lost. Some examples of suitable other components may include: heat stabilizers, weather resistance agents, a variety of stabilizers, antistatic agents, slip agents, anti-blocking agents, antifoggants, lubricants, dyes, pigments, natural oils, synthetic oils, waxes, etc. Some suitable examples of stabilizers include, antioxidants such as 2,6-di-t-butyl-4-methylphenol (BHT); phenolic antioxidants such as tetrakis[methylene-3-(3,5-di-t-butyl-4-hydroxyphenyl) propionate]methane, β-(3,5-di-t-butyl-4-hydroxyphenyl) alkyl ester propionate, and 2,2'-oxamidebis[ethyl-3-(3, 5-di-t-butyl-4hydroxyphenyl) propionate; fatty acid metal salts such as zinc stearate, calcium stearate, and calcium 1,2-hydroxystearate; polyhydric alcohol fatty acid esters such as glycidyl monostearate, glycidyl distearate, pentaerythritol monostearate, pentaerythritol distearate and pentaerythritol tristearate, etc. Furthermore, one or more different types of the components may be mixed and used in combination as well. Some examples of suitable lubricants include oleic acid amide, erucic acid amide, stearic acid amide, etc.

Furthermore, in some embodiments, the composite fiber may further include fillers such as silica, diatomaceous earth, alumina, titanium oxide, magnesium oxide, pumice powder, pumice balloon, aluminum hydroxide, magnesium hydroxide, basic magnesium carbonate, dolomite, calcium sulfate, potassium titanate, barium sulfate, calcium sulfite, talc, clay, mica, asbestos, calcium silicate, montmorillonite, bentonite, graphite, aluminum powder, and molybdenum sulfide.

Mixing of propylene type polymer and the optional components mentioned above can be achieved using any suitable conventional method.

Production of a spun-bonded nonwoven fabric can be achieved, in some embodiments, when the first propylene type polymer that forms one area of the composite fiber and the second propylene type polymer that forms the other area are melted by a separate extruder. The first propylene type polymer and the second propylene type polymer can be extruded from a nozzle plate having a composite spinning nozzle structure in such a manner that each molten material can be extruded while forming a desired fiber structure so as to extrude a composite long fiber. The long fiber extruded can be chilled by cooling air. In some embodiments, tension is applied with blowing air to form a predetermined fiber size. The fiber can be collected as is on a collection belt to deposit to form a predetermined thickness, and for bonding treatment, thermal fusion can be applied to the nonwoven fabric using embossing finish.

Where the nonwoven comprises bi-component fibers as described above, in some embodiments, the fiber size of the nonwoven fabric is preferably in the range of about 0.5 to about 5.0 denier, or any individual number within the range. In some embodiments, the fiber size can be in the range of about 1.0 to about 4.0 denier. The basis weight of the nonwoven fabric, in some embodiments, can be in the range of about 20 to about 80 g/m$^2$, or any individual number within the range. In some embodiments, the basis weight can be in the range of about 30 to about 60 g/m$^2$.

A fastening system constructed in accordance with the present invention may be incorporated into a variety of consumer and commercial goods that may benefit from having a receiving component which comprises a bond pattern constructed in accordance with the present invention. In any of the embodiments described herein, the receiving component may be a separate element added to the commercial good. For example, the receiving member may be a discrete structure joined to any component (e.g., a topsheet, an absorbent core, a backsheet, a fastening system, a side panel, a cuff, etc.) of an absorbent article or other commercial good (e.g., a wrap, a medical product, etc.). Alternatively, the receiving component may be constructed as part or all of any element of the commercial good or fastener. For example, the receiving component may be constructed as part or all of any component (e.g., a topsheet, an absorbent core, a backsheet, a fastening system, a side panel, a cuff, etc.) of an absorbent article or other commercial good (e.g., a wrap, a medical product, etc.). Further, receiving component may be disposed in any suitable location on or in the commercial good or fastener. For example, the receiving component may be disposed on a outer-facing surface of, wearer-facing surface of, or contained within the commercial good or fastener. For the sake of explanation, the receiving component of the present invention will be discussed in the context of disposable diapers.

Figure 7A:
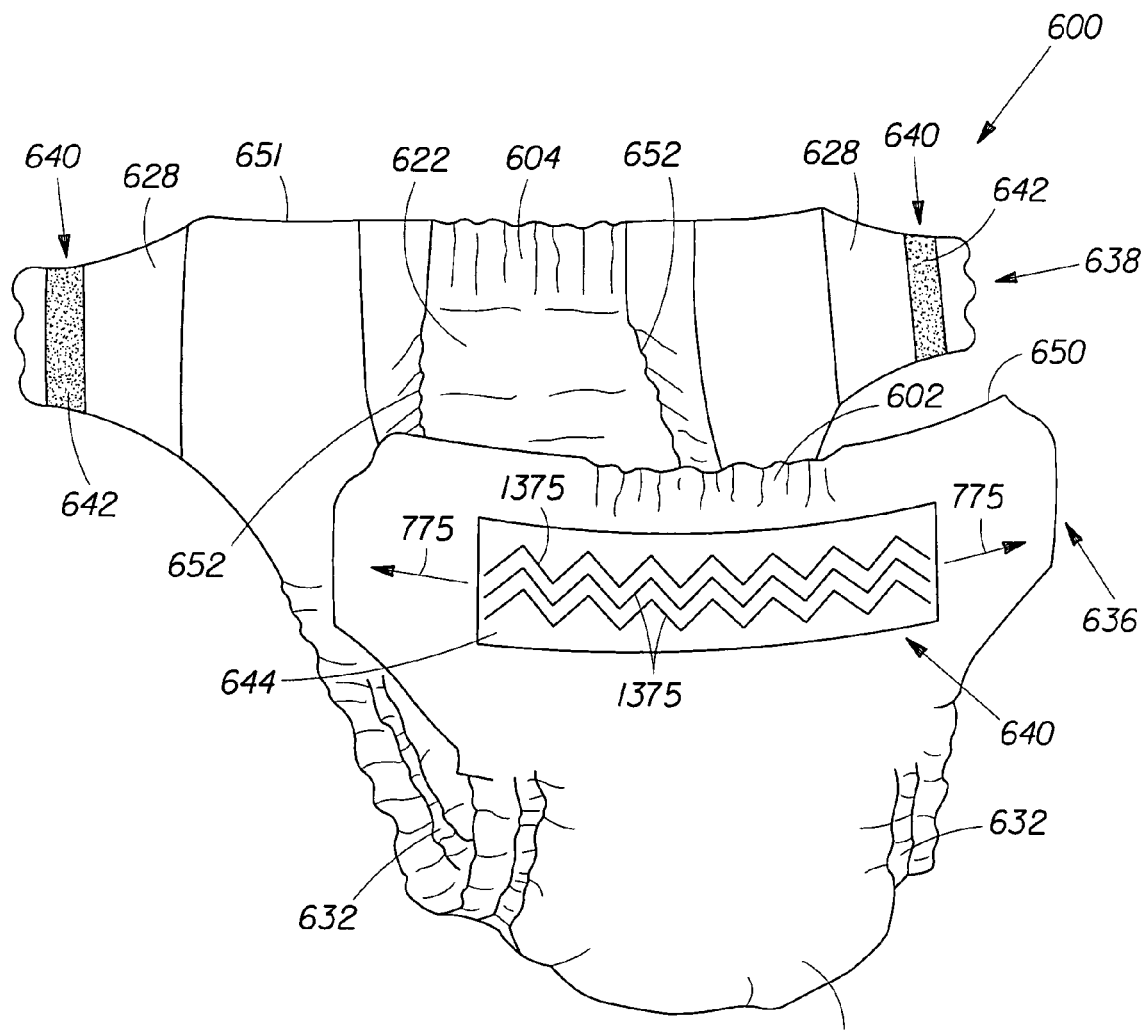
FIG. 7A is a perspective view showing a disposable absorbent article constructed in accordance with the present invention.
Figure 7B:
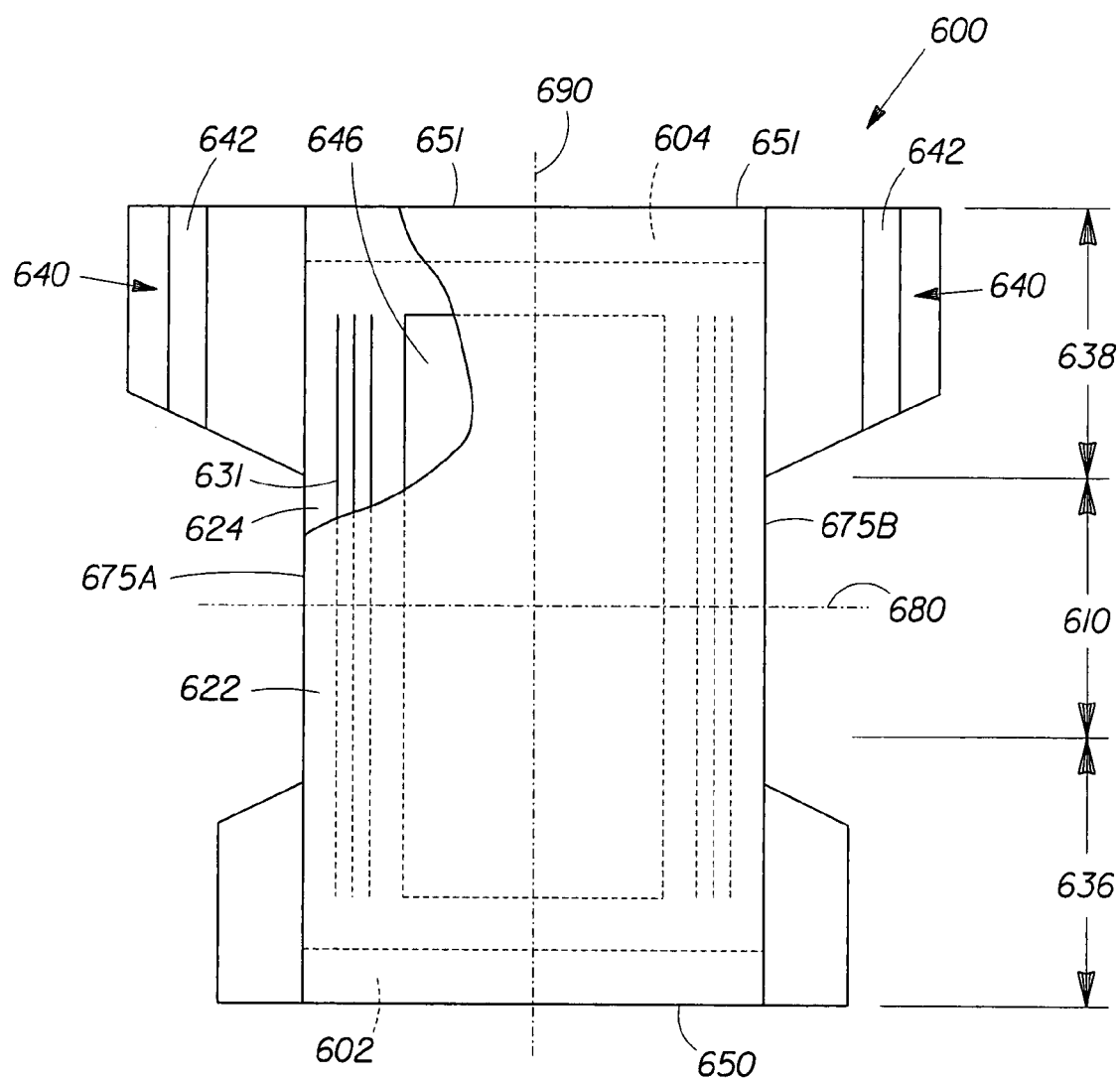
FIG. 7B is a plan view showing the disposable absorbent article of FIG. 7A in a flattened-out uncontracted state.

As shown in FIGS. 7A and 7B, a disposable absorbent article 600 may comprise a liquid pervious topsheet 622 and a backsheet 624 joined to at least a portion of the topsheet 622. The disposable absorbent article 600 further comprises an absorbent core 646 positioned between the topsheet 622 and the backsheet 624. The disposable absorbent article 600 may further comprise side panels 628, outer cuffs 632, inner cuffs 652, and waist features 630.

A portion of the periphery of the disposable absorbent article 600 can be defined by the longitudinal edges 675A and 675B; the first waist edge 650, and the second waist edge 651. The longitudinal edges 675A and 675B may run generally parallel to a longitudinal centerline 690 of the disposable absorbent article 600. The first waist edge 650 and the second waist edge 651 may run generally parallel to a lateral centerline 680 of the disposable absorbent article 600. The disposable absorbent article 600 may further comprise elastic leg features 631 which can be disposed adjacent to the longitudinal edges 675A and 675B.

The disposable absorbent article 600 may further comprise a first waist member 602 and a second waist member 604. The first waist member 602 and/or the second waist member 604 can be elastically extensible. As shown, in some embodiments, the first waist member 602 can be disposed adjacent the first waist edge 650. In some embodiments, the second waist member 604 can be disposed adjacent to the second waist edge 651. Generally, the first waist member 602 and/or the second waist member 604 can be under tension prior to joining to the disposable absorbent article 600. So, upon release of at least a portion of the tension applied to the first waist member 602 and/or the second waist member 604, a portion of the disposable absorbent article 600 joined thereto can corrugate. This corrugation of the disposable absorbent article 600 can allow the first waist member 602 and/or the second waist member 604 and the disposable absorbent article 600 to expand and contract about the waist of a wearer, thereby providing more comfort and improved fit to a wearer. Examples of suitable waist members 602 and/or 604 include those described in U.S. Pat. No. 4,515,595, U.S. Pat. No. 5,151,092, and U.S. Pat. No. 5,221,274. Although disposable diapers are generally constructed so as to have two elastic waist features, one positioned in a first waist region and one positioned in a second waist region, diapers can be constructed with a single elastic waist feature.

The disposable absorbent article 600 may further comprise outer cuffs 632 and inner cuffs 652 to improve containment of liquids and other body exudates. Each elasticized outer cuff 632 may include several different embodiments for reducing the leakage of body exudates in the leg regions. Outer cuffs 632 and inner cuffs 652 are further described in U.S. Pat. No. 3,860,003; U.S. Pat. No. 4,909,803; and U.S. Pat. No. 4,695,278.

As stated previously, the disposable absorbent article may further comprise a pair of side panels 628. As shown in FIG. 7B, the side panels 628 can extend outward from the first longitudinal edge 675A and the second longitudinal edge 675B of the disposable absorbent article 600. In some embodiments, the side panels 628 can be joined to the disposable absorbent article 600 in the second waist region 638, and in some embodiments, the side panels 628 can be joined to the disposable absorbent article 600 in the first waist region 636. Alternatively, in some embodiments, the disposable absorbent article 600 may comprise a pair of side panels which are disposed in the second waist region 638 and a pair of side panels which are disposed in the first waist region 636. In some embodiments, the side panels 628 can form a portion of the leg openings when the disposable absorbent article 600 is fastened. The side panels 628 can form a portion of the leg openings which would be disposed on an outer surface of a leg of a wearer. A crotch region 610 of the disposable absorbent article 600 in conjunction with the first waist region 636 and the second waist region 638 can form a portion of the leg openings which would be disposed on an inner surface of the leg of the wearer. In some embodiments, the side panels 628 can be elastically extensible.

The disposable absorbent article 600 further comprises a fastening system 640 which joins at least a portion of a first waist region 636 with at least a portion of a second waist region 638, preferably to form leg and waist openings. The fastening system 640 also works with the waist members(s) 602 and/or 604 to maintain lateral tension in order to keep the disposable absorbent article 600 in place about the waist of the wearer. The fastening system 640 may comprise engaging components 642 which, in some embodiments, can be disposed on the side panels 628. The fastening system 640 may further comprise a receiving component 644 which, in some embodiments, is disposed in the first waist region 636.

Figure 7C:
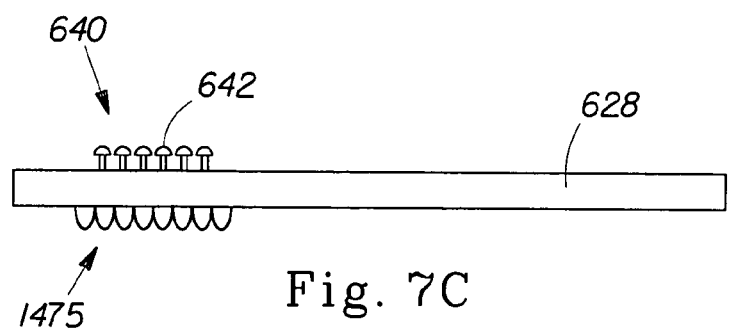
FIG. 7C is an elevation view showing another embodiment of a side panel of the disposable absorbent article of FIG. 7A.

As shown in FIG. 7C, in other embodiments, the fastening system 640 can include a plurality of fastening components on the side panels 628. For example, as shown, the side panel 628 may comprise the engaging component 642 which, in some embodiments, can include a plurality of engaging elements. Additionally, in some embodiments, the side panel 628 may further comprise a receiving component 1475 which is disposed opposite of the engaging component 642. One advantage of this arrangement is that the engaging component 642 can engage the receiving component 644 (shown in FIG. 7A) which is joined to the first waist region 636 or can join to the receiving component 1475 of the other side panel 628.

As shown in FIG. 7A, the receiving component 644 is disposed on the disposable absorbent article 600 such that the overlap of the bond lines 1375 is generally perpendicular to the primary direction of shear 775. As shown in FIG. 7A, the primary direction of shear 775 is an expected in use force which typically occurs once the disposable absorbent article 600 is in a fastened state. In some embodiments, the receiving component 644 can be disposed adjacent the first waist edge 650 in the first waist region 636 on an outer-facing surface of disposable absorbent article 600. In other embodiments, the receiving component 644 can be disposed adjacent the second waist edge 651 in the second waist region 638. In this embodiment, the engaging elements 642 can be disposed adjacent the first waist region 636. In some embodiments, receiving components 644 can be disposed on the side panels 628 and the engaging component can be disposed in the first waist region 636. In some embodiments, the receiving component 644 may comprise a plurality of discrete elements.

Any suitable engaging element 642 can be used in the present invention. An example of a suitable engaging element 642 comprises hook fastening material. The hook fastening material can mechanically engage fibrous elements of the receiving element 644 so as to provide a secure closure. A hook fastening material according to the present invention may be manufactured from a wide range of materials. Suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087.

The fastening system 640 may be the primary fastening system for joining the first and second waist regions 636 and 638. However, the fastening system 640 may be used alone or in conjunction with other fastening means such as tab and slot fasteners, tape fasteners, snaps, buttons, and the like to provide different fastening characteristics. For example, the fastening system 640 may provide the disposable absorbent article 600 with a disposal means for fastening the disposable absorbent article 600 in a configuration convenient for disposal. Further, secondary fastening means may provide the disposable absorbent article 600 with a means for adjusting fit or may increase the strength of the connection between the first waist region 636 and the second waist region 638.

The fastening system 640 can be prefastened in a package such that a caregiver or wearer may pull on the disposable absorbent article 600 when removed from the package. Alternatively, the fastening system 640 can be unfastened in the package such that the caregiver or wearer fastens the fastening system 640 while donning the disposable absorbent article 600. In yet another embodiment, a package may comprise both prefastened and unfastened disposable absorbent articles 600 for the convenience of the caregiver or the wearer.

Figure 8A:
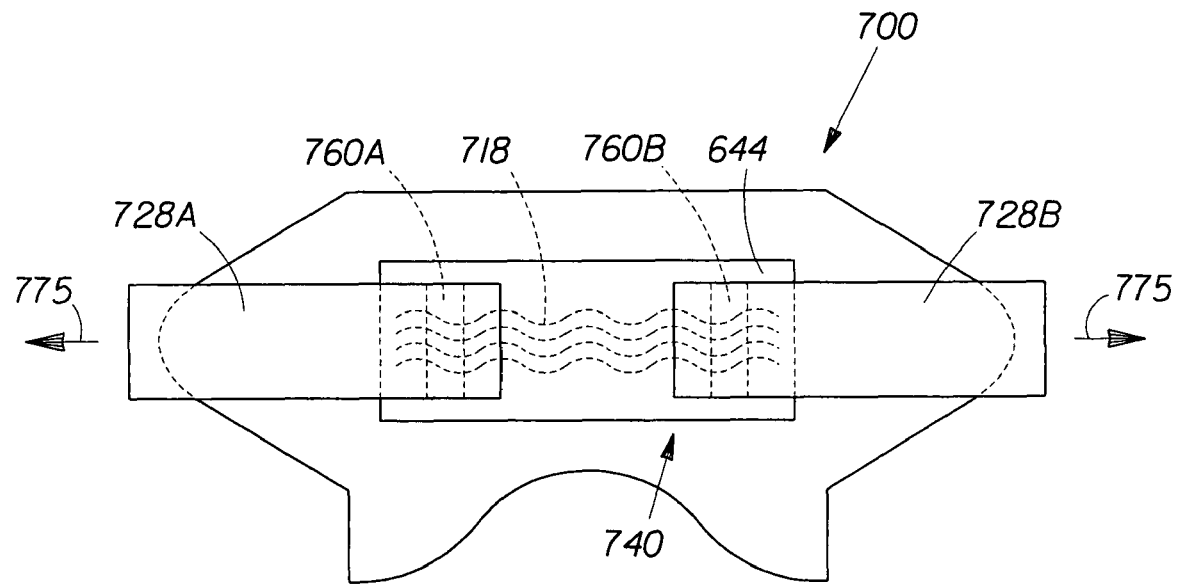
FIG. 8A is an elevation view showing a portion of the disposable absorbent article of FIG. 6 having its fastening system in a fastened state.

As shown in FIG. 8A, a disposable absorbent article 700 comprising a fastening system 740 is shown. The fastening system 740 comprises a first engaging component 760A disposed on a first side panel 728A and a second engaging component 760B disposed on a second side panel 728B. The first engaging component 760A and the second engaging component 760B can engage the receiving component 644 when fastened.

The receiving component 644 may comprise a plurality of bond lines 718 created in accordance with the present invention. Each of the plurality of bond lines 718 may comprise hills and valleys. As mentioned previously, the receiving component 644 can be disposed on the disposable absorbent article 700 such that the overlap between the bond lines is generally perpendicular to the primary direction of shear 775. So, receiving components of the present invention constructed similar to the receiving component 100 (shown in FIGS. 1B and 3) can be disposed on the disposable absorbent article 700 such that the lateral axis 162 (shown in FIGS. 1B and 3) of the receiving component is generally parallel to the primary direction of shear 775. Alternatively, receiving components of the present invention constructed similar to the receiving component 1000 (shown in FIG. 6) can be disposed on the disposable absorbent article 700 such that the longitudinal axis 1060 of the receiving component is generally parallel to the primary direction of shear 775.

The primary direction of shear 775 is defined by the in use forces. Specifically, when the disposable absorbent article 700 is in a fastened state, the first side panel 728A and the second side panel 728B exert a force on the receiving component 644. The force can be caused, in part, by the elastomeric material of the side panels, if they are elastically extensible. Additionally, the shear forces may be caused by user or caregiver during application of the disposable absorbent article 700.

Figure 8B:
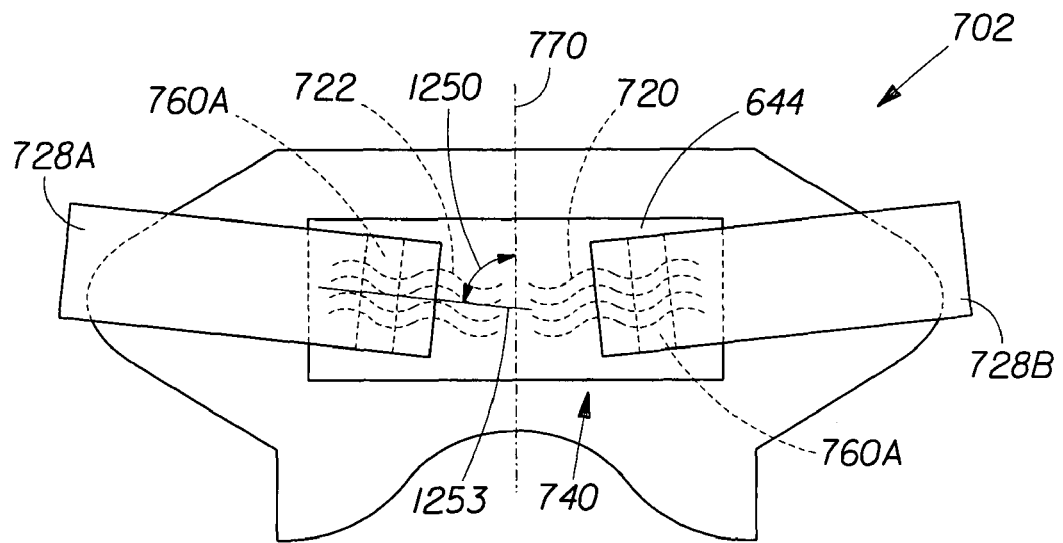
FIG. 8B is an elevation view showing a portion of the disposable absorbent article of FIG. 7 having its fastening system in a fastened state, wherein a receiving component of the fastening system is disposed on the disposable absorbent article to provide a visual alignment aid.

As shown in FIG. 8B, a disposable absorbent article 702 comprising a fastening system 740 is shown. Similar to the disposable absorbent article above, the first engaging component 760A and the second engaging component 760B can engage the receiving component 644 when fastened. The receiving component 644 may comprise a first plurality of bond lines 722 and a second plurality of bond lines 720. A portion of each of the first plurality of bond lines 722 overlaps a portion of each adjacent bond line. Similarly, a portion of each of the second plurality of bond lines 720 overlaps a portion of each adjacent bond line.

The first plurality of bond lines 722 may be angled such that they can provide a visual signal to a wearer of where to fasten the first engaging component 760A. Additionally, the second plurality of bond lines 720 may be angled such that they can provide a visual signal to a wearer of where to fasten the second engaging component 760B.

In some embodiments, the fastening angles 1250 can be in a range from between about 0 degrees to about 45 degrees or any individual number within that range. In other embodiments, the fastening angle 1250 can be between about 10 degrees and about 25 degrees. In yet other embodiments, the fastening angle 1250 can be between about 15 degrees and about 20 degrees.

The fastening angle 1250 of the first plurality of bond lines 722 can be determined by performing straight line approximations for each of the bond lines within bond pattern of the first plurality of bond lines 722. A bond line can be considered to be a part of the first plurality of bond lines 722 if a portion of that bond line overlaps any portion of another bond line within the first plurality of bond lines 722. The straight line approximations for each of the bond lines within the first plurality of bond lines 722 can be averaged to determine a first orientation line 1253 for the first plurality of bond lines 722. The intersection between the first orientation line 1253 and a longitudinal axis 770 of the disposable absorbent article 702 defines the fastening angle 1250. The same analysis can be performed for the second plurality of bond lines 720.

Disposable absorbent articles may comprise many components, elements, members, etc. and can be constructed in a variety of manners. For example, the topsheet 622 (shown in FIG. 6) and the backsheet 624 (shown in FIG. 6) can have length and width dimensions generally larger than those of the absorbent core 626 (shown in FIG. 6). The topsheet 622 (shown in FIG. 6) and the backsheet 624 (shown in FIG. 6) can extend beyond the edges of the absorbent core 626 (shown in FIG. 6), thereby forming the periphery of the disposable absorbent article 600 (shown in FIG. 6). The topsheet 622 (shown in FIG. 6), the backsheet 624 (shown in FIG. 6), and the absorbent core 626 (shown in FIG. 6) may include many different materials and may be assembled in a variety of well known configurations, exemplary diaper materials and configurations are described generally in U.S. Pat. No. 3,860,003, U.S. Pat. No. 5,151,092, and U.S. Pat. No. 5,221,274.

Any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643. Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173.

Further, the topsheet may be fully or partially elastically extensible or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775.

A suitable backsheet for use in the disposable absorbent article of the present invention may comprise a laminated structure. For example, as previously discussed, the backsheet may comprise a first backsheet layer and a second backsheet layer (see items 241 and 242 of FIG. 2C). The second backsheet layer can be impervious to liquids (e.g., urine) and comprise a thin plastic film such as a thermoplastic film having a thickness, for example, of about 0.012 mm (0.5 mils) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and U.S. Pat. No. 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

The backsheet may be joined to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements joined directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. No. 5,941,864; U.S. Pat. No. 5,977,430; and U.S. Pat. No. 6,013,063.

Embodiments of the present invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173.

Embodiments of the present invention may include a dusting layer which is well known in the art. Examples of suitable dusting layers are discussed in U.S. Pat. No. 4,888,231.

Test Methods:

Determining the Bonded Area of a Receiving Component:

Sample Preparation

1. Enough representative absorbent articles are selected from the retail packaging of the absorbent article to conduct all required tests. The receiving components of each of the absorbent articles are removed from the articles. Suitable methods include cutting the receiving components off of the articles.
2. Each sample is allowed to equilibrate in a controlled environment. The environmental parameters are 22 degrees C.±2 degrees C., 50% Relative Humidity± 10% Relative Humidity. Samples are placed in these conditions at least 24 hours prior to testing.
3. Secure a sample to a flat surface. The sample is secured to the flat surface such that the sample is completely disposed on the flat surface. The sample is secured to the flat surface using tape such as Scotch Removable Magic Tape™ manufactured by 3M™.
4. Identify the bond zone in accordance with the description of the bond zone described herein.
5. Identify the sweep regions within the bond zone in accordance with the description of the sweep regions described herein. Each of the sweep regions has a length which is equal to the contact area between the calendering rolls. Each of the sweep regions has a width which is equal to the width of the web the receiving component is produced on. Where the contact area between the calendering rolls is unavailable, divide the length of the bond zone by 0.25 and round up to the nearest whole number. The quotient is the number of sweep regions within the bond zone. The sweep regions have an equal lengths.
6. Measure the area bonded within each sweep region, and record the sweep region bonded areas as Bi, where i=1 to n with n being the total number of sweep regions. The bonded area is measured to the nearest 0.01 mm$^2$.
7. Measure the total area of each sweep region, and record the total sweep region area Si, where i=1 to n with n being the total number of sweep regions. The total area is measured to the nearest 0.01 mm$^3$.
8. From the data collected, calculate:
    a) Bond Ratio:
        i) Identify the sweep region having the smallest bond area, record as Bi,min.
        ii) Identify the sweep region having the largest bond area, record as Bi,max.
        iii) Calculate the Bond Ratio= Bi,max/Bi,min.
    b) % Bonded Area in each Sweep Region:
        i) Percent Bonded area for each sweep region=100*Bi/Si.
    c) Overall % Bonded Area:
        i) Calculate cumulative bonded area, Bt=sum of Bi, where i=1 to n.
        ii) Calculate cumulative total area, St=sum of Si, where i=1 to n.
        iii) Overall Percent Bonded Area=100*Bt/St.

As stated previously, the areas may be measured using straight-line measures and geometric/trigonometric relationships. Alternatively, computerized image analysis may be used for more complex bond line patterns.

Determining the Number of Crimps in a Fiber:

Number of crimps was measured according to the procedure explained below. It should be noted that with the exception of the procedure shown below, measurements were done according to the specification of JIS L 1015.

First, lines with a spatial separation of 25 mm were formed on a piece of glossy paper with a smooth surface. The two ends of each fiber were carefully removed from the nonwoven fabric prior to thermal compression treatment by an embossing roll such that crimping was not lost and were applied onto the aforementioned paper with a relaxation of 25±5% for the spatial separation.

The aforementioned each test piece was applied to the chuck of the crimping tester, the paper was removed, and the distance between chucks (spatial distance) (mm) during the initial load (0.18 mN×displayed tex number) was read.

The number of crimps at the time was counted and the number of crimps per distance of 25 mm was obtained and the mean value of 20 times was used. The number of crimps was obtained as the total peaks and valleys were counted and divided by 2.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A mechanical fastening system comprising:
    an engaging component comprising a plurality of engaging elements; and
    a receiving component having a longitudinal axis and a lateral axis, wherein the plurality of engaging elements are capable of engaging the receiving component, the receiving component further comprising:
        a.) a first bond line and a second bond line extending in a first direction, wherein the second bond line is disposed adjacent to the first bond line such that a portion of the second bond line overlaps a portion of the first bond line, wherein the overlap is generally parallel to a second direction, and wherein the first direction is generally perpendicular to the second direction;
        b.) a bond zone circumscribing the first bond line and the second bond line; and
        c.) a plurality of consecutive sweep regions disposed within the bond zone, each sweep region comprising a length and a width, wherein lengths of the sweep regions are equal and are generally parallel to the longitudinal axis, wherein lengths of the sweep region are greater than or equal to about 0.1 mm and less than or equal to about 1.2 mm, wherein the widths of the sweep regions are equal and are generally parallel to the lateral axis,
    wherein at least one sweep region comprises a portion of both the first bond line and the second bond line, wherein the remaining sweep regions of the plurality of sweep regions comprise at least a portion of the first bond line or at least a portion of the second bond line, wherein each sweep region has a bonded area, and wherein the receiving component has a bond ratio between two sweep regions which is greater than or equal to about 1 and less than or equal to about 20.

2. The receiving component of claim 1, wherein the first direction is generally parallel to the longitudinal axis of the receiving component.

3. The receiving component of claim 1, wherein the bond ratio is greater than or equal to about 1.0 and less than about 10.

4. The receiving component of claim 1, wherein the bond ratio is greater than or equal to about 1.0 and less than about 3.

5. The receiving component of claim 1 further comprising a nonwoven web.

6. The receiving component of claim 5, wherein the nonwoven web comprises at least 1 layer of fibers.

7. The receiving component of claim 1, wherein the each of the plurality of sweep regions has a leading edge and a trailing edge, wherein the leading edge and the trailing edge are generally parallel to the first direction, and wherein an intersection of a bond line with the trailing edge creates an angle which is greater than or equal to about 45 degrees.

8. The receiving component of claim 7, wherein the angle is greater than or equal to about 65 degrees.

9. The receiving component of claim 7, wherein the angle is greater than or equal to about 75 degrees.

10. The receiving component of claim 1, wherein the receiving component has an overall bonded area which is less than or equal to about 40%.

11. The receiving component of claim 10, wherein the bonded area in any sweep region is less than about 60%.

12. The receiving component of claim 10, wherein the overall bonded area is less than about 30% and the bonded area in any sweep region is less than about 50%.

13. The receiving component of claim 10, wherein the overall bonded area is between about 20% to about 30% and the bonded area in any sweep region is less than about 40%.

14. The receiving component of claim 1, wherein the first direction is generally parallel to the lateral axis of the receiving component.

15. A mechanical fastening system comprising:
an engaging component comprising a plurality of engaging elements; and
a receiving component having a longitudinal axis and a lateral axis, wherein the plurality of engaging elements are capable of engaging the receiving component, the receiving component further comprising:
  a.) a first bond line and a second bond line generally extending in first direction, wherein the second bond line is disposed adjacent to the first bond line such that a portion of the second bond line overlaps a portion of the first bond line, wherein the overlap is generally parallel to a second direction, and wherein the first direction is generally parallel to the second direction;
  b.) a bond zone circumscribing the first bond line and the second bond line; and
  c.) a plurality of consecutive sweep regions disposed within the bond zone, each sweep region extending in a direction generally parallel to the longitudinal axis, each sweep region comprising a length and a width, wherein the lengths of the sweep regions are equal, wherein the widths of the sweep regions are equal,
wherein at least one sweep region comprises a portion of both the first bond line and the second bond line, wherein the remaining sweep regions comprise at least a portion of the first bond line or at least a portion of the second bond line, wherein each sweep region comprises a bonded area, and wherein the receiving component has an overall bonded area which is less than or equal to about 40%, and wherein the bonded area in any sweep region is less than about 60%.

16. The receiving component of claim 15, wherein the overall bonded area is less than about 30% and the bonded area in any sweep region is less than about 50%.

17. The receiving component of claim 15, wherein the overall bonded area is between about 20% to about 30% and the bonded area in any sweep region is less than about 40%.

* * * * *

UNITED STATES PATENT AND TRADEMARK OFFICE
CERTIFICATE OF CORRECTION

PATENT NO. : 7,895,718 B2
APPLICATION NO. : 11/710216
DATED : March 1, 2011
INVENTOR(S) : Horn et al.

It is certified that error appears in the above-identified patent and that said Letters Patent is hereby corrected as shown below:

Column 29

Line 41, delete "$mm^3$" and insert --$mm^2$--.

Signed and Sealed this
Twenty-second Day of November, 2011

David J. Kappos
*Director of the United States Patent and Trademark Office*